(12) United States Patent
Rearick et al.

(10) Patent No.: US 10,100,357 B2
(45) Date of Patent: Oct. 16, 2018

(54) WINDOWED SEQUENCING

(71) Applicant: LIFE TECHNOLOGIES CORPORATION, Carlsbad, CA (US)

(72) Inventors: Todd Rearick, Cheshire, CT (US); Mark James Milgrew, Branford, CT (US); Jonathan Schultz, Guilford, CT (US); Chris Papalias, South San Francisco, CA (US); Kim L. Johnson, Carlsbad, CA (US)

(73) Assignee: Life Technologies Corporation, Carlsbad, CA (US)

( * ) Notice: Subject to any disclaimer, the term of this patent is extended or adjusted under 35 U.S.C. 154(b) by 87 days.

(21) Appl. No.: 15/043,296

(22) Filed: Feb. 12, 2016

(65) Prior Publication Data
US 2016/0168634 A1    Jun. 16, 2016

Related U.S. Application Data

(63) Continuation of application No. 13/891,023, filed on May 9, 2013, now abandoned.

(51) Int. Cl.
 *C12Q 1/68* (2018.01)
 *G06F 19/22* (2011.01)
 *C12Q 1/6874* (2018.01)

(52) U.S. Cl.
 CPC ........... *C12Q 1/6874* (2013.01); *G06F 19/22* (2013.01)

(58) Field of Classification Search
None
See application file for complete search history.

(56) References Cited

U.S. PATENT DOCUMENTS

| | | |
|---|---|---|
| 4,086,642 A | 4/1978 | Yoshida et al. |
| 4,411,741 A | 10/1983 | Janata |
| 4,437,969 A | 3/1984 | Covington et al. |
| 4,438,354 A | 3/1984 | Haque et al. |
| 4,444,644 A | 4/1984 | Hiramoto et al. |
| 4,490,678 A | 12/1984 | Kuisl et al. |
| 4,641,084 A | 2/1987 | Komatsu |
| 4,660,063 A | 4/1987 | Anthony |
| 4,691,167 A | 9/1987 | Vlekkert et al. |
| 4,701,253 A | 10/1987 | Ligtenberg et al. |
| 4,722,830 A | 2/1988 | Urie et al. |
| 4,743,954 A | 5/1988 | Brown |
| 4,764,797 A | 8/1988 | Shaw et al. |
| 4,777,019 A | 10/1988 | Dandekar |
| 4,822,566 A | 4/1989 | Newman |
| 4,863,849 A | 9/1989 | Melamede |
| 4,864,229 A | 9/1989 | Lauks et al. |
| 4,874,499 A | 10/1989 | Smith et al. |
| 4,893,088 A | 1/1990 | Myers et al. |
| 4,927,736 A | 5/1990 | Mueller et al. |
| 4,971,903 A | 11/1990 | Hyman |
| 5,009,766 A | 4/1991 | Lauks |
| 5,038,192 A | 8/1991 | Bonneau et al. |
| 5,110,441 A | 5/1992 | Kinlen et al. |
| 5,113,870 A | 5/1992 | Rossenfeld |
| 5,126,759 A | 6/1992 | Small et al. |
| 5,138,251 A | 8/1992 | Koshiishi et al. |
| 5,140,393 A | 8/1992 | Hijikihigawa et al. |
| 5,142,236 A | 8/1992 | Maloberti et al. |
| 5,151,587 A | 9/1992 | Machida et al. |
| 5,151,759 A | 9/1992 | Vinal |
| 5,164,319 A | 11/1992 | Hafeman et al. |
| 5,202,576 A | 4/1993 | Liu et al. |
| 5,284,566 A | 2/1994 | Cuomo et al. |
| 5,317,407 A | 5/1994 | Michon |
| 5,319,226 A | 6/1994 | Sohn et al. |
| 5,407,854 A | 4/1995 | Baxter et al. |
| 5,436,149 A | 7/1995 | Barnes |
| 5,439,839 A | 8/1995 | Jang |
| 5,466,348 A | 11/1995 | Holm-Kennedy |
| 5,475,337 A | 12/1995 | Tatsumi |
| 5,490,971 A | 2/1996 | Gifford et al. |
| 5,554,339 A | 9/1996 | Cozzette et al. |
| 5,583,462 A | 12/1996 | Grasshoff |
| 5,587,894 A | 12/1996 | Naruo |
| 5,593,838 A | 1/1997 | Zanzucchi et al. |
| 5,600,451 A | 2/1997 | Maki |
| 5,627,403 A | 5/1997 | Bacchetta et al. |
| 5,631,704 A | 5/1997 | Dickinson et al. |
| 5,637,469 A | 6/1997 | Wilding et al. |
| 5,646,558 A | 7/1997 | Jamshidi |
| 5,702,964 A | 12/1997 | Lee |
| 5,793,230 A | 8/1998 | Chu et al. |
| 5,846,708 A | 12/1998 | Hollis et al. |
| 5,894,284 A | 4/1999 | Garrity et al. |
| 5,907,765 A | 5/1999 | Lescouzeres et al. |
| 5,911,873 A | 6/1999 | McCarron et al. |
| 5,912,560 A | 6/1999 | Pasternak |
| 5,922,591 A | 7/1999 | Anderson et al. |
| 5,923,421 A | 7/1999 | Rajic et al. |
| 5,944,970 A | 8/1999 | Rosenblatt |
| 5,958,703 A | 9/1999 | Dower et al. |

(Continued)

FOREIGN PATENT DOCUMENTS

| | | |
|---|---|---|
| CN | 1582334 | 2/2005 |
| CN | 1585896 | 2/2005 |

(Continued)

OTHER PUBLICATIONS

Izuru, Shinmura, "Kojien", published by *Owanami, Fourth Edition*, 1991, p. 2683.

(Continued)

*Primary Examiner* — Kiajiang Zhang

(57) ABSTRACT

In one implementation, a method is described. The method includes determining an operational characteristic of sensors of a sensor array. The method further includes selecting a group of sensors in the array based on the operational characteristic of sensors in the group. The method further includes enabling readout of the sensors in the selected group. The method further includes receiving output signals from the enabled sensors, the output signals indicating chemical reactions occurring proximate to the sensors of the sensor array.

20 Claims, 7 Drawing Sheets

(56) References Cited

U.S. PATENT DOCUMENTS

| | | |
|---|---|---|
| 5,965,452 A | 10/1999 | Kovacs |
| 6,002,299 A | 12/1999 | Thomsen |
| 6,021,172 A | 2/2000 | Fossum et al. |
| 6,107,032 A | 8/2000 | Kilger et al. |
| 6,191,444 B1 | 2/2001 | Clampitt et al. |
| 6,195,585 B1 | 2/2001 | Karunasiri et al. |
| 6,210,891 B1 | 4/2001 | Nyren et al. |
| 6,255,678 B1 | 7/2001 | Sawada et al. |
| 6,274,320 B1 | 8/2001 | Rothberg et al. |
| 6,275,061 B1 | 8/2001 | Tomita |
| 6,280,586 B1 | 8/2001 | Wolf et al. |
| 6,294,133 B1 | 9/2001 | Sawada et al. |
| 6,327,410 B1 | 12/2001 | Walt et al. |
| 6,353,324 B1 | 3/2002 | Uber, III et al. |
| 6,355,431 B1 | 3/2002 | Chee et al. |
| 6,361,671 B1 | 3/2002 | Mathies et al. |
| 6,372,291 B1 | 4/2002 | Hua et al. |
| 6,384,684 B1 | 5/2002 | Redman-White |
| 6,403,957 B1 | 6/2002 | Fodor et al. |
| 6,406,848 B1 | 6/2002 | Bridgham et al. |
| 6,413,792 B1 | 7/2002 | Sauer et al. |
| 6,429,027 B1 | 8/2002 | Chee et al. |
| 6,432,360 B1 | 8/2002 | Church |
| 6,433,386 B1 | 8/2002 | Yun et al. |
| 6,459,398 B1 | 10/2002 | Gureshnik et al. |
| 6,465,178 B2 | 10/2002 | Chappa et al. |
| 6,475,728 B1 | 11/2002 | Martin et al. |
| 6,482,639 B2 | 11/2002 | Snow et al. |
| 6,485,944 B1 | 11/2002 | Church et al. |
| 6,490,220 B1 | 12/2002 | Merritt et al. |
| 6,499,499 B2 | 12/2002 | Dantsker et al. |
| 6,511,803 B1 | 1/2003 | Church et al. |
| 6,518,024 B2 | 2/2003 | Choong et al. |
| 6,518,146 B1 | 2/2003 | Singh et al. |
| 6,535,824 B1 | 3/2003 | Mansky et al. |
| 6,537,881 B1 | 3/2003 | Park et al. |
| 6,538,593 B2 | 3/2003 | Yang et al. |
| 6,545,620 B2 | 4/2003 | Groeneweg |
| 6,571,189 B2 | 5/2003 | Jensen et al. |
| 6,602,702 B1 | 8/2003 | Anslyn et al. |
| 6,605,428 B2 | 8/2003 | Kilger et al. |
| 6,613,513 B1 | 9/2003 | Kopf-Sill et al. |
| 6,618,083 B1 | 9/2003 | Chen et al. |
| 6,624,637 B1 | 9/2003 | Pechstein |
| 6,627,154 B1 | 9/2003 | Goodman et al. |
| 6,654,505 B2 | 11/2003 | Bridgham et al. |
| 6,671,341 B1 | 12/2003 | Kinget et al. |
| 6,682,899 B2 | 1/2004 | Bryan et al. |
| 6,682,936 B2 | 1/2004 | Kovacs |
| 6,686,638 B2 | 2/2004 | Fischer et al. |
| 6,700,814 B1 | 3/2004 | Nahas et al. |
| 6,703,660 B2 | 3/2004 | Yitzchaik et al. |
| 6,716,629 B2 | 4/2004 | Hess et al. |
| 6,762,022 B2 | 7/2004 | Makarov et al. |
| 6,770,472 B2 | 8/2004 | Manalis et al. |
| 6,795,006 B1 | 9/2004 | Delight et al. |
| 6,806,052 B2 | 10/2004 | Bridgham et al. |
| 6,828,100 B1 | 12/2004 | Ronaghi |
| 6,831,994 B2 | 12/2004 | Bridgham et al. |
| 6,841,128 B2 | 1/2005 | Kambara et al. |
| 6,859,570 B2 | 2/2005 | Walt et al. |
| 6,878,255 B1 | 4/2005 | Wang et al. |
| 6,888,194 B2 | 5/2005 | Yoshino |
| 6,898,121 B2 | 5/2005 | Chien et al. |
| 6,906,524 B2 | 6/2005 | Chung et al. |
| 6,919,211 B1 | 7/2005 | Fodor et al. |
| 6,926,865 B2 | 8/2005 | Howard |
| 6,929,944 B2 | 8/2005 | Matson |
| 6,939,451 B2 | 9/2005 | Zhao et al. |
| 6,953,958 B2 | 10/2005 | Baxter et al. |
| 6,969,488 B2 | 11/2005 | Bridgham et al. |
| 6,998,274 B2 | 2/2006 | Chee et al. |
| 7,008,550 B2 | 3/2006 | Li et al. |
| 7,019,305 B2 | 3/2006 | Eversmann et al. |
| 7,022,288 B1 | 4/2006 | Boss |
| 7,033,754 B2 | 4/2006 | Chee et al. |
| 7,049,645 B2 | 5/2006 | Sawada et al. |
| 7,060,431 B2 | 6/2006 | Chee et al. |
| 7,067,886 B2 | 6/2006 | Bonges et al. |
| 7,084,641 B2 | 8/2006 | Brederlow et al. |
| 7,085,502 B2 | 8/2006 | Shushakov et al. |
| 7,087,387 B2 | 8/2006 | Gerdes et al. |
| 7,091,059 B2 | 8/2006 | Rhodes |
| 7,097,973 B1 | 8/2006 | Zenhausern |
| 7,105,300 B2 | 9/2006 | Parce et al. |
| 7,106,089 B2 | 9/2006 | Nakano et al. |
| 7,173,445 B2 | 2/2007 | Fujii et al. |
| 7,190,026 B2 | 3/2007 | Lotfi et al. |
| 7,192,745 B2 | 3/2007 | Jaeger |
| 7,193,453 B2 | 3/2007 | Wei et al. |
| 7,211,390 B2 | 5/2007 | Rothberg E |
| 7,223,540 B2 | 5/2007 | Pourmand et al. |
| 7,226,734 B2 | 6/2007 | Chee et al. |
| 7,235,389 B2 | 6/2007 | Lim et al. |
| 7,238,323 B2 | 7/2007 | Knapp et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,264,934 B2 | 9/2007 | Fuller |
| 7,265,929 B2 | 9/2007 | Umeda et al. |
| 7,267,751 B2 | 9/2007 | Gelbart et al. |
| 7,276,749 B2 | 10/2007 | Martin et al. |
| 7,282,370 B2 | 10/2007 | Bridgham et al. |
| 7,285,384 B2 | 10/2007 | Fan et al. |
| 7,291,496 B2 | 11/2007 | Holm-Kennedy |
| 7,297,518 B2 | 11/2007 | Quake et al. |
| 7,298,475 B2 | 11/2007 | Gandhi et al. |
| 7,303,875 B1 | 12/2007 | Bock et al. |
| 7,317,216 B2 | 1/2008 | Holm-Kennedy |
| 7,317,484 B2 | 1/2008 | Dosluoglu et al. |
| 7,323,305 B2 | 1/2008 | Leamon et al. |
| 7,335,762 B2 | 2/2008 | Rothberg et al. |
| 7,359,058 B2 | 4/2008 | Kranz et al. |
| 7,361,946 B2 | 4/2008 | Johnson et al. |
| 7,363,717 B2 | 4/2008 | Ekseth et al. |
| 7,381,936 B2 | 6/2008 | Tan et al. |
| 7,394,263 B2 | 7/2008 | Pechstein et al. |
| 7,419,636 B2 | 9/2008 | Aker et al. |
| 7,425,431 B2 | 9/2008 | Church et al. |
| 7,455,971 B2 | 11/2008 | Chee et al. |
| 7,462,452 B2 | 12/2008 | Williams et al. |
| 7,462,512 B2 | 12/2008 | Levon et al. |
| 7,465,512 B2 | 12/2008 | Wright et al. |
| 7,466,258 B1 | 12/2008 | Akopyan et al. |
| 7,470,352 B2 | 12/2008 | Eversmann et al. |
| 7,482,153 B2 | 1/2009 | Okada et al. |
| 7,482,677 B2 | 1/2009 | Lee et al. |
| 7,499,513 B1 | 3/2009 | Tetzlaff et al. |
| 7,515,124 B2 | 4/2009 | Yaguma et al. |
| 7,575,865 B2 | 8/2009 | Leamon et al. |
| 7,576,037 B2 | 8/2009 | Engelhardt et al. |
| 7,595,883 B1 | 9/2009 | El Gamal et al. |
| 7,605,650 B2 | 10/2009 | Forbes |
| 7,608,810 B2 | 10/2009 | Yamada |
| 7,609,093 B2 | 10/2009 | Sarig et al. |
| 7,609,303 B1 | 10/2009 | Lee et al. |
| 7,612,817 B2 | 11/2009 | Tay |
| 7,614,135 B2 | 11/2009 | Santini, Jr. et al. |
| 7,667,501 B2 | 2/2010 | Surendranath et al. |
| 7,733,401 B2 | 6/2010 | Takeda |
| 7,785,790 B1 | 8/2010 | Church et al. |
| 7,842,377 B2 | 11/2010 | Lanphere et al. |
| 7,842,457 B2 | 11/2010 | Berka et al. |
| 7,859,029 B2 | 12/2010 | Lee et al. |
| 7,885,490 B2 | 2/2011 | Heideman et al. |
| 7,888,708 B2 | 2/2011 | Yazawa et al. |
| 7,923,240 B2 | 4/2011 | Su |
| 7,932,034 B2 | 4/2011 | Esfandyarpour et al. |
| 7,948,015 B2 | 5/2011 | Rothberg et al. |
| 7,955,995 B2 | 6/2011 | Kakehata et al. |
| 7,960,776 B2 | 6/2011 | Kim et al. |
| 7,981,362 B2 | 7/2011 | Glezer et al. |
| 8,012,690 B2 | 9/2011 | Berka et al. |
| 8,017,938 B2 | 9/2011 | Gomez et al. |

(56) References Cited

U.S. PATENT DOCUMENTS

| | | |
|---|---|---|
| 8,035,175 B2 | 10/2011 | Shim et al. |
| 8,067,731 B2 | 11/2011 | Matyjaszczyk et al. |
| 8,072,188 B2 | 12/2011 | Yorinobu et al. |
| 8,124,936 B1 | 2/2012 | Lagna |
| 8,133,698 B2 | 3/2012 | Silver |
| 8,138,496 B2 | 3/2012 | Li et al. |
| 8,199,859 B2 | 6/2012 | Zerbe et al. |
| 8,217,433 B1 | 7/2012 | Fife |
| 8,227,877 B2 | 7/2012 | Lee et al. |
| 8,231,831 B2 | 7/2012 | Hartzell et al. |
| 8,232,813 B2 | 7/2012 | Burdett et al. |
| 8,247,849 B2 | 8/2012 | Fife et al. |
| 8,248,356 B2 | 8/2012 | Chen |
| 8,262,900 B2 | 9/2012 | Rothberg et al. |
| 8,263,336 B2 | 9/2012 | Rothberg et al. |
| 8,264,014 B2 | 9/2012 | Rothberg et al. |
| 8,269,261 B2 | 9/2012 | Rothberg et al. |
| 8,293,082 B2 | 10/2012 | Rothberg et al. |
| 8,306,757 B2 | 11/2012 | Rothberg et al. |
| 8,313,625 B2 | 11/2012 | Rothberg et al. |
| 8,313,639 B2 | 11/2012 | Rothberg et al. |
| 8,317,999 B2 | 11/2012 | Rothberg et al. |
| 8,340,914 B2 | 12/2012 | Gatewood et al. |
| 8,343,856 B2 | 1/2013 | Therrien et al. |
| 8,349,167 B2 | 1/2013 | Rothberg et al. |
| 8,357,547 B2 | 1/2013 | Lee et al. |
| 8,361,713 B2 | 1/2013 | Bridgham et al. |
| 8,415,716 B2 | 4/2013 | Rothberg et al. |
| 8,426,898 B2 | 4/2013 | Rothberg et al. |
| 8,426,899 B2 | 4/2013 | Rothberg et al. |
| 8,435,395 B2 | 5/2013 | Rothberg et al. |
| 8,441,044 B2 | 5/2013 | Rothberg et al. |
| 8,445,194 B2 | 5/2013 | Drmanac et al. |
| 8,445,945 B2 | 5/2013 | Rothberg et al. |
| 8,449,824 B2 | 5/2013 | Sun |
| 8,450,781 B2 | 5/2013 | Rothberg et al. |
| 8,470,164 B2 | 6/2013 | Rothberg et al. |
| 8,492,800 B2 | 7/2013 | Rothberg et al. |
| 8,496,802 B2 | 7/2013 | Rothberg et al. |
| 8,502,278 B2 | 8/2013 | Rothberg et al. |
| 8,519,448 B2 | 8/2013 | Rothberg et al. |
| 8,524,057 B2 | 9/2013 | Rothberg et al. |
| 8,530,941 B2 | 9/2013 | Rothberg et al. |
| 8,535,513 B2 | 9/2013 | Rothberg et al. |
| 8,552,771 B1 | 10/2013 | Jordan et al. |
| 8,558,288 B2 | 10/2013 | Rothberg et al. |
| 8,575,664 B2 | 11/2013 | Rothberg et al. |
| 8,592,154 B2 | 11/2013 | Rearick |
| 8,653,567 B2 | 2/2014 | Fife |
| 8,658,017 B2 | 2/2014 | Rothberg et al. |
| 8,673,627 B2 | 3/2014 | Nobile et al. |
| 8,685,230 B2 | 4/2014 | Rothberg et al. |
| 8,685,298 B2 | 4/2014 | Rockenschaub et al. |
| 8,728,844 B1 | 5/2014 | Liu et al. |
| 8,731,847 B2 | 5/2014 | Johnson et al. |
| 8,742,469 B2 | 6/2014 | Milgrew |
| 8,742,472 B2 | 6/2014 | Rothberg et al. |
| 8,747,748 B2 | 6/2014 | Li et al. |
| 8,764,969 B2 | 7/2014 | Rothberg et al. |
| 8,766,327 B2 | 7/2014 | Milgrew |
| 8,766,328 B2 | 7/2014 | Rothberg et al. |
| 8,786,331 B2 | 7/2014 | Jordan et al. |
| 8,796,036 B2 | 8/2014 | Fife et al. |
| 8,821,798 B2 | 9/2014 | Bustillo et al. |
| 8,841,217 B1 | 9/2014 | Fife et al. |
| 8,847,637 B1 | 9/2014 | Guyton |
| 8,912,005 B1 | 12/2014 | Fife et al. |
| 8,936,763 B2 | 1/2015 | Rothberg et al. |
| 8,945,912 B2 | 2/2015 | Bashir et al. |
| 8,962,366 B2 | 2/2015 | Putnam et al. |
| 8,963,216 B2 | 2/2015 | Fife et al. |
| 8,983,783 B2 | 3/2015 | Johnson et al. |
| 9,023,674 B2 | 5/2015 | Shen et al. |
| 9,201,041 B2 | 12/2015 | Dalton et al. |
| 9,270,264 B2 | 2/2016 | Jordan et al. |
| 9,389,199 B2 | 7/2016 | Cheng et al. |
| 9,458,502 B2 | 10/2016 | Rothberg et al. |
| 2001/0007418 A1 | 7/2001 | Komatsu et al. |
| 2001/0024790 A1 | 9/2001 | Kambara et al. |
| 2002/0001801 A1 | 1/2002 | Fan et al. |
| 2002/0012930 A1 | 1/2002 | Rothberg et al. |
| 2002/0012933 A1 | 1/2002 | Rothberg et al. |
| 2002/0012937 A1 | 1/2002 | Tender et al. |
| 2002/0029971 A1 | 3/2002 | Kovacs |
| 2002/0042059 A1 | 4/2002 | Makarov et al. |
| 2002/0042388 A1 | 4/2002 | Cooper et al. |
| 2002/0050611 A1 | 5/2002 | Yitzchaik et al. |
| 2002/0085136 A1 | 7/2002 | Moon et al. |
| 2002/0086318 A1 | 7/2002 | Manalis et al. |
| 2002/0094533 A1 | 7/2002 | Hess et al. |
| 2002/0117694 A1 | 8/2002 | Migliorato et al. |
| 2002/0150909 A1 | 10/2002 | Stuelpnagel et al. |
| 2002/0168678 A1 | 11/2002 | Williams et al. |
| 2003/0020334 A1 | 1/2003 | Nozu |
| 2003/0032052 A1 | 2/2003 | Hadd et al. |
| 2003/0044799 A1 | 3/2003 | Matson |
| 2003/0044833 A1 | 3/2003 | Benchikh et al. |
| 2003/0054396 A1 | 3/2003 | Weiner |
| 2003/0064366 A1 | 4/2003 | Hardin et al. |
| 2003/0068629 A1 | 4/2003 | Rothberg et al. |
| 2003/0100102 A1 | 5/2003 | Rothberg et al. |
| 2003/0102510 A1 | 6/2003 | Lim et al. |
| 2003/0108867 A1 | 6/2003 | Chee et al. |
| 2003/0119020 A1 | 6/2003 | Stevens et al. |
| 2003/0124572 A1 | 7/2003 | Umek et al. |
| 2003/0124599 A1 | 7/2003 | Chen et al. |
| 2003/0141928 A1 | 7/2003 | Lee |
| 2003/0141929 A1 | 7/2003 | Casper et al. |
| 2003/0148301 A1 | 8/2003 | Aono et al. |
| 2003/0148344 A1 | 8/2003 | Rothberg et al. |
| 2003/0152929 A1 | 8/2003 | Howard |
| 2003/0152994 A1 | 8/2003 | Woudenberg et al. |
| 2003/0155942 A1 | 8/2003 | Thewes |
| 2003/0175990 A1 | 9/2003 | Hayenga et al. |
| 2003/0186262 A1 | 10/2003 | Cailloux |
| 2003/0211502 A1 | 11/2003 | Sauer et al. |
| 2003/0215791 A1 | 11/2003 | Garini et al. |
| 2003/0215857 A1 | 11/2003 | Kilger et al. |
| 2003/0224419 A1 | 12/2003 | Corcoran et al. |
| 2003/0231531 A1 | 12/2003 | Baxter et al. |
| 2004/0002470 A1 | 1/2004 | Keith et al. |
| 2004/0012998 A1 | 1/2004 | Chien et al. |
| 2004/0023253 A1 | 2/2004 | Kunwar et al. |
| 2004/0038420 A1 | 2/2004 | Gelbart et al. |
| 2004/0079636 A1 | 4/2004 | Hsia et al. |
| 2004/0106211 A1 | 6/2004 | Kauer et al. |
| 2004/0121354 A1 | 6/2004 | Yazawa et al. |
| 2004/0130377 A1 | 7/2004 | Takeda et al. |
| 2004/0136866 A1 | 7/2004 | Pontis et al. |
| 2004/0146849 A1 | 7/2004 | Huang et al. |
| 2004/0185484 A1 | 9/2004 | Costa et al. |
| 2004/0185591 A1 | 9/2004 | Hsiung et al. |
| 2004/0197803 A1 | 10/2004 | Yaku et al. |
| 2004/0235216 A1 | 11/2004 | Rhodes |
| 2004/0248161 A1 | 12/2004 | Rothberg et al. |
| 2005/0006234 A1 | 1/2005 | Hassibi |
| 2005/0009022 A1 | 1/2005 | Weiner et al. |
| 2005/0031490 A1 | 2/2005 | Gumbrecht et al. |
| 2005/0032076 A1 | 2/2005 | Williams et al. |
| 2005/0058990 A1 | 3/2005 | Guia et al. |
| 2005/0079510 A1 | 4/2005 | Berka et al. |
| 2005/0093072 A1 | 5/2005 | Bonges et al. |
| 2005/0093645 A1 | 5/2005 | Watanabe et al. |
| 2005/0106587 A1 | 5/2005 | Klapproth et al. |
| 2005/0142033 A1 | 6/2005 | Glezer et al. |
| 2005/0156207 A1 | 7/2005 | Yazawa et al. |
| 2005/0156584 A1 | 7/2005 | Feng |
| 2005/0181440 A1 | 8/2005 | Chee et al. |
| 2005/0189960 A1 | 9/2005 | Tajima |
| 2005/0191698 A1 | 9/2005 | Chee et al. |
| 2005/0202582 A1 | 9/2005 | Eversmann et al. |
| 2005/0206548 A1 | 9/2005 | Muramatsu et al. |
| 2005/0212016 A1 | 9/2005 | Brunner et al. |
| 2005/0221473 A1 | 10/2005 | Dubin et al. |

(56) References Cited

U.S. PATENT DOCUMENTS

| | | |
|---|---|---|
| 2005/0230245 A1 | 10/2005 | Morgenshtein et al. |
| 2005/0230271 A1 | 10/2005 | Levon et al. |
| 2005/0233318 A1 | 10/2005 | Chee et al. |
| 2005/0239132 A1 | 10/2005 | Klapproth |
| 2005/0266456 A1 | 12/2005 | Williams et al. |
| 2005/0282224 A1 | 12/2005 | Fouillet et al. |
| 2005/0285155 A1 | 12/2005 | Johnson et al. |
| 2006/0000772 A1 | 1/2006 | Sano et al. |
| 2006/0035400 A1 | 2/2006 | Wu et al. |
| 2006/0040297 A1 | 2/2006 | Leamon et al. |
| 2006/0057025 A1 | 3/2006 | Eversmann et al. |
| 2006/0057604 A1 | 3/2006 | Chen et al. |
| 2006/0073513 A1 | 4/2006 | Chee et al. |
| 2006/0134633 A1 | 6/2006 | Chen et al. |
| 2006/0141474 A1 | 6/2006 | Miyahara et al. |
| 2006/0154399 A1 | 7/2006 | Sauer et al. |
| 2006/0166203 A1 | 7/2006 | Tooke |
| 2006/0182664 A1 | 8/2006 | Peck et al. |
| 2006/0197118 A1 | 9/2006 | Migliorato et al. |
| 2006/0199193 A1 | 9/2006 | Koo et al. |
| 2006/0205061 A1 | 9/2006 | Roukes |
| 2006/0216812 A1 | 9/2006 | Okada et al. |
| 2006/0219558 A1 | 10/2006 | Hafeman et al. |
| 2006/0228721 A1 | 10/2006 | Leamon et al. |
| 2006/0246497 A1 | 11/2006 | Huang et al. |
| 2006/0269927 A1 | 11/2006 | Lieber et al. |
| 2006/0289726 A1 | 12/2006 | Paulus et al. |
| 2007/0069291 A1 | 3/2007 | Stuber et al. |
| 2007/0087401 A1 | 4/2007 | Neilson et al. |
| 2007/0092872 A1 | 4/2007 | Rothberg et al. |
| 2007/0095663 A1 | 5/2007 | Chou et al. |
| 2007/0096164 A1 | 5/2007 | Peters et al. |
| 2007/0099173 A1 | 5/2007 | Spira et al. |
| 2007/0099208 A1 | 5/2007 | Drmanac et al. |
| 2007/0117099 A1 | 5/2007 | Engelhardt et al. |
| 2007/0138132 A1 | 6/2007 | Barth |
| 2007/0172865 A1 | 7/2007 | Hardin et al. |
| 2007/0212681 A1 | 9/2007 | Shapiro et al. |
| 2007/0217963 A1 | 9/2007 | Elizarov et al. |
| 2007/0231824 A1 | 10/2007 | Chee et al. |
| 2007/0233477 A1 | 10/2007 | Halowani et al. |
| 2007/0247170 A1 | 10/2007 | Barbaro et al. |
| 2007/0250274 A1 | 10/2007 | Volkov et al. |
| 2007/0252176 A1 | 11/2007 | Shim et al. |
| 2007/0262363 A1 | 11/2007 | Tao et al. |
| 2007/0278488 A1 | 12/2007 | Hirabayashi et al. |
| 2008/0003142 A1 | 1/2008 | Link et al. |
| 2008/0012007 A1 | 1/2008 | Li et al. |
| 2008/0014589 A1 | 1/2008 | Link et al. |
| 2008/0032295 A1 | 2/2008 | Toumazou et al. |
| 2008/0035494 A1 | 2/2008 | Gomez et al. |
| 2008/0047836 A1 | 2/2008 | Strand et al. |
| 2008/0063566 A1 | 3/2008 | Matsumoto et al. |
| 2008/0085219 A1 | 4/2008 | Beebe et al. |
| 2008/0094074 A1 | 4/2008 | Kim et al. |
| 2008/0096216 A1 | 4/2008 | Quake |
| 2008/0111161 A1 | 5/2008 | Sorge et al. |
| 2008/0115361 A1 | 5/2008 | Santini et al. |
| 2008/0121946 A1 | 5/2008 | Youn et al. |
| 2008/0132693 A1 | 6/2008 | Berka et al. |
| 2008/0136933 A1 | 6/2008 | Dosluoglu et al. |
| 2008/0164917 A1 | 7/2008 | Floyd et al. |
| 2008/0176271 A1 | 7/2008 | Silver et al. |
| 2008/0185616 A1 | 8/2008 | Johnson et al. |
| 2008/0197022 A1 | 8/2008 | Suzuki et al. |
| 2008/0204048 A1 | 8/2008 | Stasiak et al. |
| 2008/0205559 A1 | 8/2008 | Iida |
| 2008/0210931 A1 | 9/2008 | Truong et al. |
| 2008/0230386 A1 | 9/2008 | Srinivasan et al. |
| 2009/0026082 A1 | 1/2009 | Rothberg et al. |
| 2009/0030117 A1 | 1/2009 | Lanphere et al. |
| 2009/0033370 A1 | 2/2009 | Sarig et al. |
| 2009/0048124 A1 | 2/2009 | Leamon et al. |
| 2009/0062132 A1 | 3/2009 | Borner |
| 2009/0075383 A1 | 3/2009 | Buschmann et al. |
| 2009/0079414 A1 | 3/2009 | Levon et al. |
| 2009/0120905 A1 | 5/2009 | Kohl et al. |
| 2009/0121258 A1 | 5/2009 | Kumar |
| 2009/0127589 A1 | 5/2009 | Rothberg et al. |
| 2009/0127689 A1 | 5/2009 | Ye et al. |
| 2009/0140763 A1 | 6/2009 | Kim |
| 2009/0149607 A1 | 6/2009 | Karim et al. |
| 2009/0156425 A1 | 6/2009 | Walt et al. |
| 2009/0170728 A1 | 7/2009 | Walt et al. |
| 2009/0194416 A1 | 8/2009 | Hsiung et al. |
| 2009/0201032 A1 | 8/2009 | Burdett et al. |
| 2009/0273386 A1 | 11/2009 | Korobeynikov et al. |
| 2010/0007326 A1 | 1/2010 | Nakazato |
| 2010/0026814 A1 | 2/2010 | Shimoda |
| 2010/0039146 A1 | 2/2010 | Park et al. |
| 2010/0052765 A1 | 3/2010 | Makino |
| 2010/0105373 A1 | 4/2010 | Kanade |
| 2010/0133547 A1 | 6/2010 | Kunze et al. |
| 2010/0137143 A1 | 6/2010 | Rothberg et al. |
| 2010/0156454 A1 | 6/2010 | Weir |
| 2010/0176463 A1 | 7/2010 | Koizumi et al. |
| 2010/0188073 A1 | 7/2010 | Rothberg et al. |
| 2010/0197507 A1 | 8/2010 | Rothberg et al. |
| 2010/0244106 A1 | 9/2010 | Parker et al. |
| 2010/0273166 A1 | 10/2010 | Garcia Tello |
| 2010/0282617 A1 | 11/2010 | Rothberg et al. |
| 2010/0300895 A1 | 12/2010 | Nobile et al. |
| 2010/0301398 A1 | 12/2010 | Rothberg et al. |
| 2011/0037121 A1 | 2/2011 | Lee et al. |
| 2011/0062972 A1 | 3/2011 | Je et al. |
| 2011/0114827 A1 | 5/2011 | Yamaoka et al. |
| 2011/0165557 A1 | 7/2011 | Ah et al. |
| 2011/0169056 A1 | 7/2011 | Wey et al. |
| 2011/0181253 A1 | 7/2011 | Isham et al. |
| 2011/0230375 A1 | 9/2011 | Rothberg et al. |
| 2011/0236263 A1 | 9/2011 | Sawada et al. |
| 2011/0247933 A1 | 10/2011 | Rothberg et al. |
| 2011/0262903 A1 | 10/2011 | Davidson et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0287945 A1 | 11/2011 | Rothberg et al. |
| 2011/0299337 A1 | 12/2011 | Parris et al. |
| 2012/0000274 A1 | 1/2012 | Fife |
| 2012/0001056 A1 | 1/2012 | Fife et al. |
| 2012/0001236 A1 | 1/2012 | Fife et al. |
| 2012/0001237 A1 | 1/2012 | Fife et al. |
| 2012/0001615 A1 | 1/2012 | Levine |
| 2012/0001646 A1 | 1/2012 | Bolander et al. |
| 2012/0001779 A1 | 1/2012 | Fife et al. |
| 2012/0012900 A1 | 1/2012 | Lee et al. |
| 2012/0013392 A1 | 1/2012 | Rothberg et al. |
| 2012/0022795 A1 | 1/2012 | Johnson et al. |
| 2012/0034607 A1 | 2/2012 | Rothberg et al. |
| 2012/0037961 A1 | 2/2012 | Rothberg et al. |
| 2012/0040844 A1 | 2/2012 | Rothberg et al. |
| 2012/0045368 A1 | 2/2012 | Hinz et al. |
| 2012/0045844 A1 | 2/2012 | Rothberg et al. |
| 2012/0055811 A1 | 3/2012 | Rothberg et al. |
| 2012/0055813 A1 | 3/2012 | Rothberg et al. |
| 2012/0056248 A1 | 3/2012 | Fife |
| 2012/0067723 A1 | 3/2012 | Rearick et al. |
| 2012/0129703 A1 | 5/2012 | Rothberg et al. |
| 2012/0129728 A1 | 5/2012 | Rothberg et al. |
| 2012/0129732 A1 | 5/2012 | Rothberg et al. |
| 2012/0135870 A1 | 5/2012 | Rothberg et al. |
| 2012/0143531 A1 | 6/2012 | Davey et al. |
| 2012/0154018 A1 | 6/2012 | Sugiura |
| 2012/0161207 A1 | 6/2012 | Homyk et al. |
| 2012/0173159 A1 | 7/2012 | Davey et al. |
| 2012/0249192 A1 | 10/2012 | Matsushita |
| 2012/0261274 A1 | 10/2012 | Rearick et al. |
| 2012/0279859 A1 | 11/2012 | Rothberg et al. |
| 2012/0280285 A1 | 11/2012 | Rothberg et al. |
| 2012/0280286 A1 | 11/2012 | Rothberg et al. |
| 2012/0283146 A1 | 11/2012 | Rothberg et al. |
| 2012/0286332 A1 | 11/2012 | Rothberg et al. |
| 2012/0286333 A1 | 11/2012 | Rothberg et al. |

(56) References Cited

U.S. PATENT DOCUMENTS

| | | |
|---|---|---|
| 2012/0286771 A1 | 11/2012 | Rothberg et al. |
| 2012/0288853 A1 | 11/2012 | Rothberg et al. |
| 2012/0288976 A1 | 11/2012 | Rothberg et al. |
| 2012/0289413 A1 | 11/2012 | Rothberg et al. |
| 2012/0293158 A1 | 11/2012 | Rothberg et al. |
| 2012/0295795 A1 | 11/2012 | Rothberg et al. |
| 2012/0322054 A1 | 12/2012 | Rothberg et al. |
| 2012/0326213 A1 | 12/2012 | Bustillo et al. |
| 2012/0326767 A1 | 12/2012 | Milgrew |
| 2012/0329043 A1 | 12/2012 | Milgrew |
| 2012/0329044 A1 | 12/2012 | Milgrew |
| 2012/0329192 A1 | 12/2012 | Bustillo et al. |
| 2013/0001653 A1 | 1/2013 | Milgrew et al. |
| 2013/0004949 A1 | 1/2013 | Rearick |
| 2013/0009214 A1 | 1/2013 | Bustillo et al. |
| 2013/0015505 A1 | 1/2013 | Rothberg et al. |
| 2013/0015506 A1 | 1/2013 | Rothberg et al. |
| 2013/0017959 A1 | 1/2013 | Rothberg et al. |
| 2013/0105868 A1 | 5/2013 | Kalnitsky et al. |
| 2013/0210128 A1 | 8/2013 | Rothberg et al. |
| 2013/0210182 A1 | 8/2013 | Rothberg et al. |
| 2013/0210641 A1 | 8/2013 | Rothberg et al. |
| 2013/0217004 A1 | 8/2013 | Rothberg et al. |
| 2013/0217587 A1 | 8/2013 | Rothberg et al. |
| 2013/0281307 A1 | 10/2013 | Li et al. |
| 2013/0324421 A1 | 12/2013 | Rothberg et al. |
| 2013/0341734 A1 | 12/2013 | Merz |
| 2014/0080717 A1 | 3/2014 | Li et al. |
| 2014/0148345 A1 | 5/2014 | Li et al. |
| 2014/0234981 A1 | 8/2014 | Zarkesh-Ha et al. |
| 2014/0235452 A1 | 8/2014 | Rothberg et al. |
| 2014/0235463 A1 | 8/2014 | Rothberg et al. |
| 2014/0308752 A1 | 10/2014 | Chang et al. |
| 2015/0097214 A1 | 4/2015 | Chen et al. |
| 2016/0178568 A1 | 6/2016 | Cheng et al. |

FOREIGN PATENT DOCUMENTS

| | | |
|---|---|---|
| CN | 1703623 | 11/2005 |
| CN | 1826525 | 8/2006 |
| CN | 1294421 C | 1/2007 |
| CN | 101669026 | 3/2010 |
| CN | 101676714 | 3/2010 |
| DE | 4232532 | 4/1994 |
| DE | 4430811 | 9/1995 |
| DE | 19512117 | 10/1996 |
| DE | 102008012899 | 9/2009 |
| EP | 0223618 | 5/1987 |
| EP | 1243925 A2 | 9/2002 |
| EP | 1243925 A3 | 3/2003 |
| EP | 1432818 | 6/2004 |
| EP | 1542009 | 6/2005 |
| EP | 1557884 | 7/2005 |
| EP | 1870703 | 12/2007 |
| GB | 2461127 | 12/2009 |
| JP | 58070155 | 4/1983 |
| JP | 62-237349 | 10/1987 |
| JP | 02-250331 | 10/1990 |
| JP | 02-310931 | 12/1990 |
| JP | H05-080115 | 4/1993 |
| JP | 2000055874 | 2/2000 |
| JP | 2002272463 | 9/2002 |
| JP | 2003-279532 | 10/2003 |
| JP | 2004-501025 | 4/2004 |
| JP | 2005218310 | 8/2004 |
| JP | 2004-271384 | 9/2004 |
| JP | 2005077210 | 3/2005 |
| JP | 2005-515475 | 5/2005 |
| JP | 2005-518541 | 6/2005 |
| JP | 2005-207797 | 8/2005 |
| JP | 2006138846 | 6/2006 |
| JP | 2006-284225 | 10/2006 |
| JP | 2007/243003 | 9/2007 |
| JP | 2008-215974 | 9/2008 |
| JP | 2010513869 | 4/2010 |
| JP | 2011525810 | 9/2011 |
| JP | 2012-506557 | 3/2012 |
| JP | 2015-506557 | 3/2012 |
| KR | 100442838 | 8/2004 |
| KR | 100455283 | 11/2004 |
| TW | 489231 | 9/1998 |
| TW | 567326 | 8/2001 |
| TW | 200530610 | 2/2004 |
| TW | 200914857 | 1/2006 |
| TW | 201017189 | 1/2006 |
| TW | 200946904 | 11/2009 |
| WO | 1989/09283 | 10/1989 |
| WO | 1998/13523 | 4/1998 |
| WO | 1998/046797 | 10/1998 |
| WO | 2001/20039 | 3/2001 |
| WO | 2001/43498 | 6/2001 |
| WO | 2001/081896 | 11/2001 |
| WO | 2002/077287 | 10/2002 |
| WO | 2002/086162 | 10/2002 |
| WO | PCT/JP2003/04697 | 4/2003 |
| WO | 03/073088 | 9/2003 |
| WO | 2004017068 | 2/2004 |
| WO | 2004/048962 | 6/2004 |
| WO | 2005062049 | 7/2004 |
| WO | 2004081234 | 9/2004 |
| WO | 2005/015156 | 2/2005 |
| WO | 2005/022142 | 3/2005 |
| WO | 2005/043160 | 5/2005 |
| WO | 2005/047878 | 5/2005 |
| WO | 2005/054431 | 6/2005 |
| WO | 2005/062049 | 7/2005 |
| WO | 2005/073706 | 8/2005 |
| WO | 2005/084367 | 9/2005 |
| WO | 2005/090961 | 9/2005 |
| WO | 2006/005967 | 1/2006 |
| WO | 2006/022370 | 3/2006 |
| WO | 2006/056226 | 6/2006 |
| WO | 2007/002204 | 1/2007 |
| WO | 2007/086935 | 8/2007 |
| WO | 2008/007716 | 1/2008 |
| WO | 2008/058282 | 5/2008 |
| WO | 2008/076406 | 6/2008 |
| WO | 2008076406 | 6/2008 |
| WO | 2008/133719 | 11/2008 |
| WO | 2009/012112 | 1/2009 |
| WO | 2009/014155 | 1/2009 |
| WO | 2009/041917 | 4/2009 |
| WO | 2009/074926 | 6/2009 |
| WO | 2009/081890 | 7/2009 |
| WO | 2008/107014 | 9/2009 |
| WO | 2009/158006 A2 | 12/2009 |
| WO | 2009/158006 A3 | 12/2009 |
| WO | 2010/047804 A1 | 4/2010 |
| WO | 2010/047804 A8 | 4/2010 |
| WO | 2010/138182 A2 | 12/2010 |
| WO | 2010/138186 | 12/2010 |
| WO | 2010/138188 | 12/2010 |
| WO | 2010/138182 A3 | 1/2011 |
| WO | 2012/003359 | 1/2012 |
| WO | 2012/003363 | 1/2012 |
| WO | 2012/003368 | 1/2012 |
| WO | 2012/003380 | 1/2012 |
| WO | 2012/006222 | 1/2012 |
| WO | 2012/046137 | 4/2012 |
| WO | 2012/152308 | 11/2012 |
| WO | 2014/077783 | 5/2014 |

OTHER PUBLICATIONS

Nakazato, Kazuo, "An Integrated ISFET Sensor Array", *Sensors*, vol. 9 No. 11, 2009, pp. 8831-8851.

Wen-Yaw, Chung A. et al., "New ISFET interface circuit design with temperature Compensation", *CiteSeerx*—URL: http://citesserx.ist.psu.edu/viewdoc/download?doi=10.1.1.95.2321&rep=rep1&type=pdf, 2006, 1.

[No Author Listed], , "ISFET Wikipedia article", *Wikipedia*, Last modified Nov. 7, 2006, 2006.

(56) References Cited

OTHER PUBLICATIONS

Ahmadian, et al., "Single-nucleotide polymorphism analysis by pyrosequencing" *Anal. Biochem*, vol. 280, 2000, 103-110.
Akiyama, T et al., "Ion-Sensitive Field-Effect Transistors with Inorganic Gate Oxide for pH Sensing", *IEE Transactions on Electron Devices*, vol. ED-20(12), 1982, pp. 1936-1941.
AU2011226767, , "Search Information Statement", Oct. 26, 2011, pp. 1-3.
Bandiera, L. et al., "A fully electronic sensor for the measurement of cDNA hybridization kinetics", *Biosens Bioelectron*, vol. 22, 2007, pp. 2108-2114.
Barbaro, M et al., "A CMOS, Fully Integrated Sensor for Electronic Detection of DNA Hybridization", *IEEE Electron Device Letters*, vol. 27(7), 2006, pp. 595-597.
Barbaro, M. et al., "A Charge-Modulated FET for Detection of Biomolecular Processes: Conception, Modeling, and Simulation", *IEEE Transactions on Electron Devices*, vol. 53(1), 2006, pp. 158-166.
Barbaro, M. et al., "Fully electronic DNA hybridization detection by a standard CMOS biochip", *Sensors and Actuators B Chemical* vol. 118, 2006, 41-46.
Bashford, G. et al., "Automated bead-trapping apparatus and control system for singlemolecule DNA sequencing", *Optics Express*, vol. 16(5), Mar. 3, 2008, pp. 3445-3455.
Baumann, W. et al., "Microelectronic sensor system for microphysiological application on living cells", *Sensors Actuators B*, vol. 55, 1999, pp. 77-89.
Bausells, J. et al., "Ion-sensitive field-effect transistors fabricated in a commercial CMOS technology", *Sensors and Actuators B Chemical*, vol. 57, 1999, pp. 56-62.
Bergveld, "ISFET, Theory and Practice", *IEEE Sensor Conference*, Toronto, Oct. 2003, 2003, pp. 1-26.
Bergveld, "Thirty years of ISFETOLOGY What happened in the past 30 years and what may happen in the next 30 ears", *Sensors and Actuators* B vol. 88, 2003, pp. 1-20.
Besselink, et al., "ISFET Affinity Sensor", *Methods in Biotechnology*, vol. 7: *Affinity Biosensors: Techniques and Protocols*, 1998, pp. 173-185.
Bobrov, P. et al., "Chemical sensitivity of an ISFET with Ta2O5 membrane in strong acid and alkaline solutions", *Sensors and Actuators B*, vol. 3, 1991, pp. 75-81.
Bockelmann, U. et al., "Detecting DNA by field effect transistor arrays", *Proceedings of the 2006 IFIP International Conference on Very Large Scale Integration*, 2006, 164-168.
Bousse, L. et al., "A process for the combined fabrication of ion sensors and CMOS circuits", *IEEE Electron Device Letters*, vol. 9(1), 1988, pp. 44-46.
Bousse, L. et al., "Zeta potential measurements of Ta2O5 and SiO2 thin films" *J. Colloid Interface Sci.*, vol. 147(1), 1991, pp. 22-32.
Chan, Wai P. et al., "An Integrated ISFETs Instrumentation System in Standard CMOS Technology", *IEEE Journal of Solid-State Circuits*, vol. 45, No. 9, Sep. 2010, pp. 1923-1934.
Chen, Y. et al., "Nanoscale field effect transistor for biomolecular signal amplification", *App. Phy Letter*, vol. 91., 2007, pp. 243511-1-243511-3.
Chen, Y. et al., "Silicon-based nanoelectronic field-effect pH sensor with local gate control", *App Phys Letter*, vol. 89, 2006, pp. 223512-1-223512-3.
Chin, Yuan-Lung et al., "Titanium Nitride Membrane Application to Extended Gate Field Effect Transistor pH Sensor Using VLSI Technology" *Jpn. J. Appl. Phys.* vol. 40, Part 1, No. 11, Nov. 2001, pp. 6311-6315.
Chou, J. et al., "Letter to the Editor on Simulation of Ta2O5 gate ISFET temperature characteristics", *Sensors and Actuators B*, vol. 80, 2001, pp. 290-291.
Chou, J. et al., "Simulation of Ta2O5 gate ISFET temperature characteristics" *Sensor and Actuators B*, vol. 71, Letters to the Editor, 2000, pp. 73-76.

Chung, et al., "ISFET interface circuit embedded with noise rejection capability", *Electronics Letters*, vol. 40, No. 18, Oct. 2004, 1115-116.
Chung, W-Y et al., "ISFET performance enhancement by using the improved circuit techniques", *Sensors and Actuators B*, vol. 113, 2006, pp. 555-562.
Chung, W-Y et al., "New ISFET interface circuit design with temperature compensation", *Microelectronics Journals* vol. 37(10), Oct. 1, 2006, pp. 1105-1114.
Chung, W-Y et al., "Temperature compensation electronics for ISFET readout applications", *Biomedical Circuits and Systems*, IEEE International Workshop Singapore, Dec. 1, 2004, pp. 305-308.
Dazhong, Z. et al., "Research of CMOS Biosensor IC for Extracellular Electrophysiological Signal Recording and pH value Measuring", *Solid-State and Integrated-Circuit Technology, 9th International Conference*, NJ USA, Oct. 20, 2008, pp. 2557-2560.
Dorf, Richard C. , "The Electrical Engineering Handbook" University of California, Davis, *CRC Press*, 2 edition, Chapter 3—Linear Circuit Analysis, Jun. 25, 2004, pp. 3-1 to 3-66.
Eijkel, J. et al., "Measuring Donnan-related phenomena using a solid-state ion sensor and a concentration-step method", *J. Membrane Sci.*, vol. 127, 1997, pp. 203-221.
Eijkel, J. , "Potentiometric detection and characterization of adsorbed protein using stimulus-response measurement techniques", *Thesis*, Sep. 3, 1955, pp. 1-147; 160-192.
Eltoukhy, H et al., "A 0.18μm CMOS 10-6 lux Bioluminescence Detection System-on-Chip", ISSCC 2004/Session12/Biomicrosystems/12.3, 2004, pp. 1-3.
Eltoukhy, H. et al., "A. 0.18-μm CMOS Bioluminescence Detection Lab-on-Chip" *IEEE J. Solid-State Circuits*, vol. 41(3), 2006, pp. 651-662.
EP09822323.3, "European Extended Search Report" dated May 27, 2015, 8 pages.
EP10780930, "European Search Report" dated Jun. 15, 2015, 3 pages.
EP10780935, "European Search Report" dated Jun. 9, 2015, 5 pages.
EP10780935, "Supplementary European Search Report" dated Sep. 30, 2015, 6 pages.
EP10857377, "European Search Report" dated Jun. 26, 2015, 3 pages.
EP11801437.2, "European Extended Search Report" dated Jul. 25, 2013, 10 pages.
EP11801437.2, "Examination Notification" dated Feb. 12, 2015, 8 pages.
EP11801439.8, "Extended Search Report" dated Mar. 7, 2014, 9 pages.
EP11804218.3, "European Extended Search Report" dated Jul. 11, 2013, 3 pages.
EP11827128.7, "European Search Report" dated Aug. 1, 2013, 5 pages.
EP13161312.7, "Extend European Search Report" dated Oct. 15, 2013, 8 pages.
EP13163995.7, "EP Search Report" dated Jul. 9, 2014.
EP13163995.7, "Extend European Search Report" dated Aug. 20, 2013, 6 pages.
EP13174555.6, "EP Extended Search Report" dated Dec. 12, 2013, 8 pages.
EP13174555.6, "EP Search Report" dated Nov. 21, 2013, 5 pages.
EP13177039.8, "EP Search Report" dated Nov. 21, 2013, 9 pages.
EP13177590.0, "EP Search Report" dated Nov. 20, 2013, 5 pages.
EP13177590.0, "European Examination Notification" dated Sep. 8, 2014, 9 pages.
EP14152861.2, "EP Search Report" dated Jul. 7, 2014, 5 pages.
EP7867780.4, "Examination Report" dated Jul. 3, 2012.
Eriksson, J. et al., "Pyrosequencing technology at elevated temperature", *Electrophoresis*, vol. 25, 2004, pp. 20-27.
Esfandyarpour, H. et al., "Gate-controlled microfluidic chamber with magnetic bead for DNA sequencing-by-synthesis technology", *Proc 5th Intl Conf Nanochannels, Microchannels, Minnichannels*, Puebla, Mexico (Jun. 18-20, 2007), Jun. 18, 2007, pp. 1-5.

(56) References Cited

OTHER PUBLICATIONS

Eversmann, B. et al., "A 128×128 CMOS Biosensor Array for Extracellular Recording of Neural Activity", *IEEE J. Solid-State Circ.*, vol. 38(12), Dec. 12, 2003, pp. 2306-2317.
Faramarzpour, N. et al., "CMOS-Based Active Pixel for Low-Light Level Detection: Analysis and Measurements", *IEEE Trans Electron Devices*, vol. 54(12), Dec. 2007, pp. 3229-3237.
Finn, A et al., "Towards an Optimization of FET-Based Bio-Sensors", *European Cells and Materials*, vol. 4, Sup 2, 2002, pp. 21-23.
Fraden, J., "Handbook of Modern Sensors—Physics, Designs, and Applications . . . " *17.3.2 Chemfet Sensors*, 1996, pp. 499-501.
Fritz, J. et al., "Electronic detection of DNA by its intrinsic molecular charge", PNAS, vol. 99, No. 22, Oct. 2002, 14142-14146.
Gardner, J.W. et al., "Enhancing electronic nose performance by sensor selection using a new integer-based genetic algorithm approach", *Science Direct, Sensors and Actuators B*, vol. 106, 2005, pp. 114-121.
Gracia, I. et al., "Test Structures for ISFET Chemical Sensors", *Proc IEEE 1992 Intl Conf Microelec Test Struct*, vol. 5, 1992, pp. 156-159.
Hammond, et al., "Performance and system-on-chip integration of an unmodified CMOS ISFET", *Science Direct Sensors and Actuators* vol. 111-112, 2005, pp. 254-258.
Hammond, P. et al., "A System-on-Chip Digital pH Meter for Use in a Wireless Diagnostic Capsule", *IEEE Transactons on Biomedical Engineering*, vol. 52(4), 2005, pp. 687-694.
Hammond, P. et al., "Design of a Single-Chip pH Sensor Using a Conventional 0.6—μm CMOS Process", *IEEE Sensors Journal*, vol. 4(6), 2004, 706-712.
Hammond, P. et al., "Encapsulation of a liquid-sensing microchip using SU-8 photoresist", *MicoElectronic Engineering*, vol. 73-74, 2004, pp. 893-897.
Hammond, S. et al., "Genomic sequencing and analysis of a Chinese Hamster ovary cell line using Illumina sequencing technology", *BMC Genomics*, vol. 12:67, 2011, pp. 1-8.
Han, Y, "Label-free detection of biomolecules by a field-effect transistor microarray biosensor with bio-functionalized gate surfaces", Masters Dissertation, 2006, pp. 1-63.
Hanshaw, R. et al., "An indicator displacement system for fluorescent detection of phosphate oxyanions under physiological conditions", *Science Direct, Tetrahedron Letters*, vol. 45, Nov. 15, 2004, pp. 8721-8724.
Hara, H. et al., "Dynamic response of a Ta2O5-gate pH-sensitive field-effect transistor", *Sensors Actuators B*, vol. 32, 1996, pp. 115-119.
Hermon, Z. et al., "Miniaturized bio-electronic hybrid for chemical sensing applications" *Tech Connect News*, Apr. 22, 2008, pp. 1.
Hideshima, S. et al., "Detection of tumor marker in blood serum using antibody-modified field effect transistor with optimized BSA blocking", *Sensors and Actuations B: Chemical*, vol. 161, 2012, pp. 146-150.
Hijikata, et al., "Identification of a Single Nucleotide Polymorphism in the MXA Gene Promoter (T/T at nt -88) Correlated with the Response of Hepatitis C Patients to Interferon", *Intervirology*, vol. 43, 2000, 124-127.
Hizawa, et al., "Sensing Characteristics of Charge Transfer Type pH Sensor by Accumulative Operation", *IEEE Sensors. EXCO*, Daegu, Korea, Oct. 22-25, 2006, pp. 144-147.
Hizawa, T et al., "Fabrication of a two-dimensional pH image sensor using a charge transfer technique", *Sensors and Actuators B Chemical* vol. 117, 2006, 509-515.
Hizawa, T. et al., "32×32 pH Image Sensors for Real Time Observation of Biochemical Phenomena", *Transducers & Eurosensors '07*, 14th Intl. Conf. on Solid-State, Actuators and Microsystems, Lyon, France, Jun. 10-14, 2007, 2007, pp. 1311-1312.
Ingebrandt, Sven et al., "Label-free detection of DNA using field-effect transistors", *Phys. stat. sol. (a)* 2003, No. 14, 2006, pp. 3399-3411.

Jakobson, C. et al., "Low frequency noise and drift in Ion Senstive Field Effect Transistors", *Sensors Actuators B*, vol. 68, 2000, pp. 134-139.
Ji, H. et al., "A CMOS contact imager for locating individual cells", *ISCAS* 2006, pp. 3357-3360.
Ji, H. et al., "Contact Imaging: Simulation and Experiment" *IEEE Trans Circuits Systems-I: Regular Papers*, vol. 54(8), 2007, pp. 1698-1710.
Kim, D. et al., "An FET-type charger sensor for highly sensitive detection of DNA sequence", *Biosens Bioelectron*, vol. 20(1), 2004, pp. 69-74.
Klein, M., "Time effects of ion-sensitive field-effect transistors", *Sens Act B*, vol. 17, 1989, pp. 203-208.
Koch, S et al., "Protein detection with a novel ISFET-based zeta potential analyzer", *Biosensors & Bioelectronics*, vol. 14, 1999, pp. 413-421.
Krause, M. et al., "Extended gate electrode arrays for extracellular signal recordings", *Sensors and Actuators B*, vol. 70, 2000, pp. 101-107.
Kruise, J. et al., "Detection of protein concentrations using a pH-step titration method", *Sensors Actuators B*, vol. 44, 1997, pp. 297-303.
Leamon, J. et al., "A Massively Parallel PicoTiterPlate Based Platform for Discrete Picoliter-Scale Polymerase Chain Reactions", *Electrophoresis*, vol. 24, 2003, pp. 3769-3777.
Leamon, J. et al., "Cramming More Sequencing Reactions onto Microreactor Chips", *Chemical Reviews*, vol. 107, 2007, pp. 3367-3376.
Lee, C-S et al., "Ion-sensitive Field-Effect Transistor for Biological Sensing", *Sensors*, vol. 9, 2009, pp. 7111-7131.
Lee, S. et al., "An Enhanced Glucose Biosensor Using Charge Transfer Techniques", *Biosensors and Bioelectronics*, vol. 24, 2008, pp. 650-656.
Li, et al., "Sequence-Specific Label-Free DNA Sensors Based on Silico Nanowires", *Nano Letter,*, vol. 4, No. 2, 2004, 245-247.
Ligler, Frances S. et al., "Array biosensor for detection of toxins", *Anal. Bioanal Chem* vol. 377, 2003, 469-477.
Lin, B.J. et al., "Practicing the Novolac deep-UV portable conformable masking technique", *Journal of Vacuum Science and Technology*, Vo. 19 No. 4, 1981, 1313-1319.
Lohrengel, M. et al., "A new microcell or microreactor for material surface investigations at large current densities", *Electrochimica Acta*, vol. 49, 2004, pp. 2863-2870.
Lui, A. et al., "A Test Chip for ISFET/CMNOS Technology Development", *Proc. of the 1996 IEEE Intl. Conf. on Microelectronic Test Structures*, vol. 9, 1996, pp. 123-128.
Margulies, et al., "Genome sequencing in microfabricated high-density picolitre reactors", *Nature*, vol. 437 (15), Jul. 31, 2005, 376-380.
Marshall, et al., "DNA chips: an array of possibilities", *Nature Biotechnology*, vol. 16, 1998, 27-31.
Martinoia, S. et al., "A behavioral macromodel of the ISFET in SPICE", *Sensors Actuators B*, vol. 62, 2000, pp. 182-189.
Martinoia, S. et al., "Development of ISFET Array-Based Microsystems for Bioelectrochemical measurements of cell populations" *Biosensors & Bioelectronics*, vol. 16, 2001, pp. 1043-1050.
Matsuo, J. et al., "Charge Transfer Type pH Sensor with Super High Sensitivity", *the 14th. international conference on solid-state sensors actuators and microsystems*, France, Jun. 10-14, 2007, pp. 1881-1884.
Matula, Richard A., "Electrical Resistivity of Copper, Gold, Palladium, and Silver", *Journal of Physical and Chemical Reference Data*, vol. 8.4, 1979, pp. 1147-1298.
Medoro, G. et al., "A Lab-on-a-Chip for Cell Detection and Manipulation" *IEEE Sensors J*, vol. 3(3), 2003, pp. 317-325.
Meyburg, et al., "N-Channel field-effect transistors with floating gates for extracellular recordings", *Biosens Bioelectron*, vol. 21(7), 2006, pp. 1037-1044.
Milgrew, et al., "The fabrication of scalable multi-sensor arrays using standard CMOS technology", *2003 IEEE Custom Integrated Circuits Conference*, 2003, pp. 513-516.

(56) References Cited

OTHER PUBLICATIONS

Milgrew, M. et al., "A 16×16 CMOS proton camera array for direct extracellular imaging of hydrogen-ion activity", *IEEE Intl Solid-State Circuits Conf*, Session 32:24, 2008, pp. 590-591; 638.
Milgrew, M. et al., "A large transistor based sensor array chip for direct extracellular imaging", *Sensors and Actuators B Chemical*, vol. 111-112, 2005, 347-353.
Milgrew, M. et al., "Matching the transconductance characteristics of CMOS ESFET arrays by removing trapped charge", *IEEE Trans Electron Devices*, vol. 55(4), 2008, pp. 1074-1079.
Milgrew, M. et al., "Microsensor Array Technology for Direct Extracellular Imaging", Apr. 5, 2006, pp. 1-23.
Milgrew, M. et al., "The development of scalable sensor arrays using standard CMOS technology", *Sensors and Actuators B*, vol. 103 2004, 37-42.
Milgrew, M.J. et al., "The development of scalable sensor arrays using standard CMOS technology", *ScienceDirect, Sensors and Actuators*, vol. 103, 2004, pp. 37-42.
Milgrew, Mark J. et al., "A Proton Camera Array Technology for Direct Extracellular Ion Imaging", *IEEE International Symposium on Industrial Electronics*, 2008, 2051-2055.
Miyahara, Y. et al., "Biochip Using Micromachining Technology", *J. Institute of Electrostatics, Japan*, vol. 27, No. 6, 2003, 268-272.
Miyahara, Y. et al., "Direct Transduction of Primer Extension into Electrical Signal Using Genetic Field Effect Transistor", *Micro Total Analysis Systems 2004*, vol. 1, 2004, pp. 303-305.
Miyahara, Y. et al., "Potentiometric Detection of DNA Molecules Using Field Effect Transistor", *The Japan Society of Applied Physics*, No. 3 (Translation included), 2003, 1180, 30A-S2.
Naidu, M. S. et al., "Introduction to Electrical Engineering", Chapter 1—*Fundamental Concepts of Electricity, McGraw Hill Education (India) Private Limited*, 1995, pp. 1-10.
Neaman, Donald A. , "Electronic Circuit Analysis and Design", *McGraw Hill Higher Education*, 2nd edition, Chapter 6—Basic FET Amplifiers, (reference will be up loaded in 2 parts due to size) part 1 of 2, Dec. 1, 2000, pp. 313-345.
Neaman, Donald A. , "Electronic Circuit Analysis and Design", *McGraw Hill Higher Education*, 2nd edition, Chapter 6—Basic FET Amplifiers, (feference will be uploaded in 2 parts due to size) part 2 of 2, Dec. 1, 2000, pp. 346-381.
Nishiguchi, K. et al., "Si nanowire ion-sensitive field-effect transistors with a shared floating sate", *Applied Physics Letters* vol. 94, 2009, pp. 163106-1 to 163106-3.
Nyren, P. et al., "Enzymatic Method for Continuous Monitoring of Inorganic Pyrophosphate Synthesis", *Analytical Biochemistry*, vol. 151, 1985, pp. 504-509.
Oelbner, W. et al., "Encapsulation of ESFET sensor chips", *Sensors Actuators B*, vol. 105, 2005, pp. 104-117.
Oelbner, W. et al., "Investigation of the dynamic response behaviour of ISFET pH sensors by means of laser Doppler velocimetry (LDV)", *Sensors Actuators B*, vol. 26-27, 1995, pp. 345-348.
Offenhausser, A. et al., "Field-Effect transistor array for monitoring electrical activity from mammalian neurons in culture", *Biosensors & Bioelectronics*, vol. 12 (8), 1997, pp. 819-826.
Ohno, Y. et al., "Electrolyte-Gated Graphene Field-Effect Transistors for Detecting pH and Protein Adsorption", *Nano Letters*, vol. 9(9), Jul. 28, 2009, pp. 3318-3322.
Palan, B. et al., "New ISFET sensor interface circuit for biomedical applications", *Sensors and Actuators B: Chemical: International Journal Devoted to Research and Developement of Physical and Chemical Transducers*, Elsevier S.A. Ch., vol. 57, No. 1-3, 1999, 63-68.
Park, K-Y et al., "ISFET glucose sensor system with fast recovery characteristics by employing electrolysis", *Sensors and Actuators B: Chemical*, vol. 83 (1-3), Mar. 15, 2002, pp. 90-97.
Patolsky, F. et al., "Nanowire-Based Biosensors", *Analyt Chem 1*, vol. 78(13), 2006, pp. 4261-4269.
PCT/JP2005/001987, "International Search Report" dated Apr. 5, 2005.
PCT/JP2005/015522, "International Preliminary Report on Patentability", dated Mar. 19, 2007.
PCT/JP2005/015522, "International Search Report", (includes English translation) dated Sep. 27, 2005.
PCT/US/2009/05745, "International Preliminary Report on Patentability" dated Apr. 26, 2011.
PCT/US/2009/05745, "International Search Report" dated Dec. 11, 2009.
PCT/US/2009/05745, "Written Opinion" dated Dec. 11, 2009.
PCT/US2007/025721, "Declaration of Non-Establishment of International Search Report" dated Jul. 15, 2008.
PCT/US2007/025721, "International Preliminary Report on Patentability" dated Jun. 16, 2009.
PCT/US2007/025721, "Written Opinion" dated Jun. 16, 2009.
PCT/US2009/003797, "International Search Report and Written Opinion" dated Mar. 12, 2010.
PCT/US2010/001543, "International Preliminary Report on Patentability" dated Nov. 29, 2011 pp. 1-8.
PCT/US2010/001543, "International Search Report and Written Opinion" dated Oct. 13, 2010, pp. 1-12.
PCT/US2010/001553, "International Preliminary Report on Patentability" dated Dec. 8, 2011, pp. 1-10.
PCT/US2010/001553, "International Search Report and Written Opinion" dated Jul. 28, 2010, pp. 1-2.
PCT/US2010/048835, "International Preliminary Report on Patentability" dated Mar. 19, 2013, 7 pages.
PCT/US2010/48835, "International Search Report and Written Opinion" dated Dec. 16, 2010, pp. 1-12.
PCT/US2011/042655, "International Search Report" dated Oct. 21, 2011, pp. 1-2.
PCT/US2011/042660, "International Search Report" dated Nov. 2, 2011.
PCT/US2011/042665, "International Search Report" dated Nov. 2, 2011.
PCT/US2011/042668, "International Preliminary Report on Patentability" dated Mar. 26, 2013, 11 pages.
PCT/US2011/042668, "International Search Report" dated Oct. 28, 2011.
PCT/US2011/042669, "International Search Report and Written Opinion" dated Jan. 9, 2012, pp. 1-5.
PCT/US2011/042683, "International Preliminary Report on Patentability" dated Jun. 4, 2013, 5 pages.
PCT/US2011/042683, "International Search Report and Written Opinion" dated Feb. 16, 2012.
PCT/US2012/058996, "International Search Report and Written Opinion" dated Jan. 22, 2013, pp. 1-11.
PCT/US2012/071471, "International Preliminary Report on Patentability" dated Jun. 24, 2014, 8 pages.
PCT/US2012/071471, "International Search Report of the International Searching Authority and Written Opinion" dated Apr. 24, 2013, 14 pages.
PCT/US2012/071482, "International Preliminary Amendment" dated Jun. 24, 2014, 7 pages.
PCT/US2012/071482, "International Search Report of the International Searching Authority and Written Opinion" dated May 23, 2013, 11 pages.
PCT/US2013/022129, "International Preliminary Report on Patentability" dated Jul. 22, 2014, 11 pages.
PCT/US2013/022129, "International Search Report of the International Searching Authority and Written Opinion" dated Aug. 9, 2013, 18 pages.
PCT/US2013/022140, "International Preliminary Report on Patentability" dated Jul. 22, 2014, 9 pages.
PCT/US2013/022140, "International Search Report of the International Searching Authority and Written Opinion" dated May 2, 2013, 15 pages.
PCT/US2014/020887, "International Preliminary Report on Patentability" dated Sep. 15, 2015, 8 pages.
PCT/US2014/020887, "International Search Report and Written Opinion" dated May 30, 2014, 12 pages.
PCT/US2014/020892, "International Search Report and Written Opinion" dated Jun. 3, 2014.

(56) References Cited

OTHER PUBLICATIONS

PCT/US2014/040923, "International Preliminary Report on Patentability" dated Dec. 15, 2015, 8 pages.
PCT/US2014/040923, "International Search Report and Written Opinion" dated Sep. 1, 2014, 14 pages.
Poghossian, A. et al., "Functional testing and characterization of ISFETs on wafer level by means of a micro-droplet cell", *Sensors*, vol. 6, 2006, pp. 397-404.
Pollack, J. et al., "Genome-wide analysis of DNA copy-numbe changes using cDNA microarrays", *Nature Genetics, Nature America Inc.*, vol. 23, Sep. 1999, pp. 41-46.
Pourmand, N et al., "Direct electrical detection of DNA synthesis", *PNAS*, vol. 103(17), 2006, pp. 6466-6470.
Pouthas, F. et al., "Spatially resolved electronic detection of biopolymers", *Phys Rev*, vol. 70, 2004, pp. 031906-1-031906-8.
Premanode, et al., "Ultra-low power precision ISFET readout using global current feedback", *Electronic Letters*, vol. 42, No. 22, Oct. 2006, 1264-1265.
Premanode, B. et al., "A composite ISFED readout circuit employing current feedback", *Sensors Actuators B*, vol. 127, 2007, pp. 486-490.
Premanode, B. et al., "A novel, low power biosensor for real time monitoring of creatine and urea in peritoneal dialysis", *Sensors Actuators B*, vol. 120, 2007, pp. 732-735.
Premanode, B. et al., "Drift Reduction in Ion-Sensitive FETs using correlated double sampling", *Electronics Letters*, vol. 43, No. 16, Aug. 2, 2007, 857 (2 pages).
Purushothaman, S. et al., "Protons and single nucleotide polymorphism detection: A simple use for the Ion Sensitive Field Effect Transistor", *Sensors and Actuators B Chemical*, vol. 114(2), 2006, pp. 964-968.
Purushothaman, S. et al., "Towards Fast Solid State DNA Sequencing", *IEEE ISCAS 2002 Proceedings*, Circuits and Systems, vol. 4, 2002, pp. IV-169-IV-172.
Rodriguez-Villegas, E. , "Solution to trapped charge in FGMOS transistors" *Electronics Letters*, vol. 39(19), 2003.
Ronaghi, M. et al., "A Sequencing Method Based on Real-Time Pyrophosphate" *Science* vol. 281, 1998, 363-365.
Rothberg, J. et al., "An integrated semiconductor device enabling non-optical genome sequencing", *Nature*, vol. 475, No. 7356, Jul. 21, 2011, pp. 348-352.
Rowe, Chris A. et al., "An Array Immunosensor for Simultaneous Detection of Clinical Analytes", *Anal. Chem.* vol. 71, 1999, pp. 433-439.
Sakata, et al., "Potentiometric Detection of DNA Using Genetic Transistor", *Denki Gakkai Kenkyukai Shiryo Chemical Sensor Kenkyukai*, CHS-03-51-55, 2003, 1-5.
Sakata, T. et al., "Cell-based field effect devices to cell adhesion analysis", *Intl. Conf. on Microtechnologies in Medicine and Biology*, May 9-12, 2006, Okinawa, Japan, 2006, pp. 177-179.
Sakata, T. et al., "Detection of DNA recognition events using multi-well field effect transistor", *Biosensors and Bioelectronics* vol. 21, 2005, pp. 827-832.
Sakata, T. et al., "Detection sensitivity of genetic field effect transistor combined with charged nanoparticle-DNA conjugate", *Proc. of 2006 Intl. Conf. on Microtechnologies in Medicine and Biology*, May 9-12 2005 Okinawa, Japan, 2006, pp. 97-100.
Sakata, T. et al., "Direct detection of single nucleotide polymorphism using genetic field effect transistor", *Digest of Papers Microprocesses and Nanotechnology 2004*, Osaka, Japan, 2004 International Microprocesses and Nanotechnology Conference, 2004, pp. 226-227.
Sakata, T. et al., "Direct Detection of Single-Base Extension Reaction Using Genetic Field Effect Transistor", *Proc. of 3rd Ann. Intl. IEEE EMBS Special Topic Conf. on Microtechnologies in Medicine and Biology*, Kahuku, Oahu, HI, May 12-15, 2005, 2005, pp. 219-222.
Sakata, T. et al., "DNA Analysis Chip Based on Field-Effect Transistors" *Japanese Journal of Applied Physics*, vol. 44(4B), 2005, pp. 2854-2859.
Sakata, T. et al., "DNA Sequencing Based on Intrinsic Molecular Charges", *Angewandte Chemie International Edition 2006*, vol. 118, 2006, 2283-2286.
Sakata, T. et al., "DNA Sequencing Using Genetic Field Effect Transistor", *13th Intl. Conf. on Solid-State Sensors, Actuators and Microsystems*, Jun. 5-9, 2005, Seoul, Korea, 2005, pp. 1676-1679.
Sakata, T. et al., "Immobilization of oligonucleotide probes on Si3N4 surface and its application to genetic field effect transistor", *Materials Science and Engineering: C*, vol. 24, 2004, pp. 827-832.
Sakata, T. et al., "Potential Behavior of Biochemically Modified Gold Electrode for Extended-Gate Field-Effect Transistor", *Japanese Journal of Applied Physics*, vol. 44(4B), 2005, pp. 2860-2863.
Sakata, T. et al., "Potential Response of Genetic Field Effect Transistor to Charged Nanoparticle-DNA Conjugate", *Digest of Papers Microprocesses and Nanotechnology 2005*, Tokyo, Japan, 2005 Intl Microprocesses and Nanotech Conference, Hotel Bellclassic, 2005, pp. 42-43.
Sakata, T. et al., "Potentiometric Detection of Allele Specific Oligonucleotide Hybridization Using Genetic Field Effect Transistor", *Micro Total Analysis Systems 2004*, 8th Intl. Conf. on Miniaturized Systems for Chemistry and Life Sciences, Sep. 26-30, 2004, Malmo, Sweden, 2004, pp. 300-302.
Sakata, T. et al., "Potentiometric Detection of DNA Molecules Hybridization Using Gene Field Effect Transistor and Intercalator", *Materials Research Society Symposium Proceedings*, vol. 782, Micro- and Nanosystems, Dec. 1-3, 2003, Boston, Massachusetts, 2004, pp. 393-398.
Sakata, T. et al., "Potentiometric Detection of Single Nucleotide Polymorphism by Using a Genetic Field-effect transistor", *ChemBioChem*, vol. 6, 2005, pp. 703-710.
Sakurai, T. et al., "Real-Time Monitoring of DNA Polymerase Reactions by a Micro ISFET pH Sensor", *Anal Chem*, vol. 64(17), 1992, pp. 1996-1997.
Salama, K. , "CMOS luminescence detection lab-on-chip: modeling, design, and characterization", *Thesis*, Presented at Stanford University, 2005, pp. ii-78.
Salama, K. , "Modeling and simulation of luminescence detection platforms" *Biosensors & Bioelectronics*, 2004, pp. 1377-1386.
Sawada, K. et al., "A novel fused sensor for photo- and ion-sensing" *Sensors Actuators B*, vol. 106, 2005, pp. 614-618.
Sawada, K. et al., "Highly sensitive ion sensors using charge transfer technique", *Sensors Actuators B*, vol. 98, 2004, pp. 69-72.
Schasfoort, R. et al., "A new approach to immunoFET operation", *Biosensors & Bioelectronics*, vol. 5, 1990, pp. 103-104.
Schasfoort, R. et al., "Field-effect flow control for microfabricated fluidic networks", *Science*, vol. 286(5441), 1999, pp. 942-945.
Schoning, M. et al., "Bio FEDs (Field-Effect Devices): State-of-the-Art and New Directions", *Electroanalysis*, vol. 18(19-20), 2006, pp. 1893-1900.
Seong-Jin, K. et al., "Label-Free CMOS DNA Quantification With On-Chip Noise Reduction Schemes", *Solid-State Sensors, Actuators and Microsystems Conference, IEEE*, Jun. 10, 2013, pp. 947-950.
SG200903992-6 "Search and Examination Report (Favourable) dated Jan. 20, 2011", 12.
Shah, N. , "Microfabrication of a parellel-array DNA pyrosequencing chip", *NNIN REU Research Accomplishments*, 2005, pp. 130-131.
Shepherd, L. et al., "A biochemical translinear principle with weak inversion ISFETs", *IEEE Trans Circuits Syst—I*, vol. 52(12), Dec. 2005, pp. 2614-2619.
Shepherd, L. et al., "A novel voltage-clamped CMOS ISFET sensor interface", *IEEE*, 2007, pp. 3331-3334.
Shepherd, L. et al., "Towards direct biochemical analysis with weak inversion ISFETS", *Intl Workshop on Biomedical . . .* , 2004, S1.5-5-S1.5-8.
Shepherd, L. et al., "Weak inversion ISFETs for ultra-low power biochemical sensing and real-time analysis", *Sensors Actuators B*, vol. 107, 2005, pp. 468-473.
Shi, Y. et al., "Radical Capillary Array Electrophoresis Microplace and Scanner for High-Performance Nucleic Acid Analysis", *Anal. Chem.*, vol. 71(23), 1999, 5354-5361.

(56) References Cited

OTHER PUBLICATIONS

Simonian, A. L. et al., "FET based biosensors for the direct detection of organophosphate neurotoxins", *Electroanalysis*, vol. 16(22), 2004, pp. 1896-1906.
Souteyrand, E. et al., "Direct detection of the hybridization of synthetic homo-oligomer DNA sequences by field effect", *J Phys Chem B*, vol. 101(15), 1997, pp. 2980-2985.
Starodub, N. et al., "Immunosensor for the determination of the herbicide simazine based on an ion-selective field-effect transistor", *Analytica Chimica Acta*, vol. 424, 2000, pp. 37-43.
Takenaka, et al., "DNA Sensing on a DNA Probe-Modified Electrode Using Ferrocenylnaphthalene Dimide as the Electrochemically Active Ligand", *Anal. Chem.*, vol. 72, No. 6, 2000, 1334-1341.
Temes, G.C. et al., "A Tutorial Discussion of the Oversampling Method for A/D and D/A Conversion", *1990 IEEE International Symposium on Circuits and Systems*, vol. 2 of 4, 1990, 5 pages.
Thewes, R. et al., "CMOS-based Biosencor Arrays", *Proceedings of the Design, Automation and Test in Europe Conference and Exhibition*, 2005, 2 pages.
Tokuda, T. et al., "A CMOS image sensor with optical and potential dual imaging function for on-chip bioscientific applications", *Sensors and Actuators A*, vol. 125, No. 2, 2006, 273-280.
Tomaszewski, D. et al., "Electrical characterization of ISFETs" *J Telecomm Info Technol*, Mar. 2007, pp. 55-60.
Toumazou, C. et al., "Using transistors to linearase biochemistry" *Electronics Letters*, vol. 43(2), Jan. 18, 2007, 3 pages.
Truman, P., "Monitoring liquid transport and chemical composition in lab on . . . ", *Lab on a Chip*, vol. 6, 2006, pp. 1220-1228.
Uslu, F. et al., "Labelfree fully electronic nucleic acid detection system based on a field-effect transistor device", *Biosens & Bioelectron*, vol. 19(12), 2004, pp. 1723-1731.
Van Der Schoot, Bart et al., "The Use of a Multi-ISFET Sensor Fabricated in a Single Substrate", *Letter to the Editors, Sensors and Actuators*, vol. 12 1987, pp. 463-468.
Van Der Wouden, E. et al., "Directional flow induced by synchronized longitudinal and zeta-potential controlling AC-electrical fields", *Lab Chip*, vol. 6(10), 2006, pp. 1300-1305.
Van Hal, R.E.G. et al., "A general model to describe the electrostatic potential at electrolyte oxide interfaces", *Advances in Colloid and Interface Science*, vol. 69, 1996, pp. 31-62.
Van Kerkhof, "The Development of an ISFET based heparin sensor using the ion-step measuring method", *Biosensors and Bioelectronics*, vol. 9, Nos. 9-10, 1993, 463-472.
Van Kerkhof, "The Development of an ISFET-based Heparin Sensor", *Thesis*, 1994.
Van Kerkhof, J et al., "The ISFET based heparin sensor with a monolayer of protamine as affinity ligand", *Biosensors & Bioelectronics*, vol. 10(3), 1995, pp. 269-282.
Van Kerkhof, J. et al., "ISFET Responses on a stepwise change in electrolyte concentration at constant pH", *Sensors Actuators B: Chemical* vol. 18-19, 1994, pp. 56-59.
Vardalas, John, "Twists and Turns in the Development of the Transistor" *IEEE-USA Today's Engineer Online*, May 2003, 6 pages.
Voigt, H. et al., "Diamond-like carbon-gate pH-ISFET" *Sensors and Actuators B.*, vol. 44, 1997, pp. 441-445.
Wagner, T et al., "'All-in-one' solid-state device based on a light-addressable potentiometric sensor platform", *Sensors and Actuators B*, vol. 117, 2006, pp. 472-479.
Wang, W. et al., "Label-free detection of small-molecule-protein interactions by using nanowire nanosensors", *Proc. of the Natl. Acad.of Sciences (PNAS)*, vol. 102(9), 2005, pp. 3208-3212.
Wilhelm, D. et al., "pH Sensor Based on Differential Measurements on One pH-FET Chip", *Sensors and Actuators B*, vol. 4, 1991, pp. 145-149.
Woias, P, "Modelling the short time response of ISFET sensors" *Sensors and Actuators B*, vol. 24-25, 1995, pp. 211-217.
Woias, P. et al., "Slow pH response effects of silicon nitride ISFET sensors", *Sensors and Actuators B*, vol. 48, 1998, pp. 501-504.
Wood, et al., "Base composition-independent hybridization in tetramethylammonium chloride: a method for oligonucleotide screening of highly complex gene libraries", *Proceedings of the National Academy of Sciences*, vol. 82, 1985, 1585-1588.
Wu, P. et al., "DNA and protein microarray printing on silicon nitride waveguide surfaces", *Biosensens Bioelectron*, vol. 21(7), 2006, pp. 1252-1263.
Xu, J-J et al., "Analytical Aspects of FET-Based Biosensors", *Frontiers in Bioscience*, vol. 10, 2005, pp. 420-430.
Yeow, T.C.W. et al., "A very large integrated pH-ISFET sensor array chip compatible with standard CMOS processes", *Sensor and Actuators B*, vol. 44, 1997, 434-440.
Yoshida, Shoji et al., "Development of a Wide Range pH Sensor based on Electrolyte-Insulator-Semiconductor Structure with Corrosion-Resistant Al2O3—Ta2O5 and Al2O3—ZrO2", *Journal of the Electrochemical Society* vol. 151(3), 2004, pp. H53-H58.
Yuqing, M. et al., "Ion sensitive field effect trnasducer-based biosensors", *Biotechnology Advances*, vol. 21, 2003, pp. 527-534.
Zhang, X. et al., "32-Channel Full Customized CMOS Biosensor Chip for Extracellular neural Signal Recording", *Proc. of the 2nd Intl. IEEE EMBs Conf. on Neural Engineering*, Arlington, Virginia, 2005, pp. v-viii.
Zhao, B. et al., "Floating-Gate Ion Sensitive Field-Effect Transistor for Chemical and Biological Sensing", *MRS Proceedings*, vol. 828, 2005, pp. 349-354.
Zhou, et al., "Quantitative detection of single nucleotide polymorphisms for a pooled sample by a bioluminometric assay coupled with modified primer extension reactions (BAMPER)" *Nuc. Acids Res.*, vol. 29(19), e93, 2001, 1-11.
Schroder, Dieter K., "6. Oxide and Interface Trapped Charges, Oxide Thickness", *Semiconductor Material and Device Characterization, John Wiley & Sons*, ISBN: 978-0-471-73906-7, Feb. 17, 2006, pp. 319-387.
OV5640 Datasheet Product Specification, *¼" color CMOS QSXGA (5 megapixel) image sensor with OmniBSI technology*, May 1, 2011, p. 1, line 9 and pp. 2-7, paragraph 1.
International Search Report and Written Opinion of the International Searching Authority for International Application No. PCT/US2015/066023 dated Mar. 14, 2016, 18 pages.
International Search Report and Written Opinion of the International Searching Authority for International Application No. PCT/US2015/066052 dated Apr. 7, 2016, 19 pages.
Liu, Yan et al., "An ISFET based sensing array with sensor offset compensation and pH enhancement", *Proc. of 2010 IEEE Int. Symp. on Circuits and Systems (ISCAS)*, ISBN:978-1-4244-5308-5, Jun. 2, 2010, pp. 2283-2286.
Morgenshtein, Arkadiy et al., "Wheatstone-Bridge readout interface for ISFET/REFET application", *Sensors and Actuators B: Chemical*, vol. 1, Mar. 2004, pp. 18-27.
Moriizumi, Toyosaka, "Biosensors", *Oyo Bututi (monthly publication of the Japan Society of Applied Physics)*, vol. 54, No. 2, Feb. 10, 1985, pp. 98-114.
Nakazato, Kazuro et al., "28p-Y-7 ISFET sensor array integrated circuits based on CMOS process", *The 55th annual meeting of the Japan Society of Applied Physics, book of Abstracts*, ISBN:978-4-903968-44-5, Mar. 27, 2008, p. 70.
Nakazato, Kazuro, "An Integrated ISFET Sensor Array", *Sensors*, Nov. 2009, vol. 9, No. 11, ISSN:1424-8220, [online], Internet, URL, http://www.mdpi.com/1424-8220/9/11/8831/pdf, Nov. 2008, pp. 8831-8851.

WINDOWED SEQUENCING

CROSS-REFERENCE TO RELATED APPLICATIONS

This application is a continuation of U.S. patent application Ser. No. 13/891,023 filed May 9, 2013, the entire contents of which is incorporated by reference herein in its entirety.

FIELD OF THE INVENTION

This disclosure, in general, relates to methods for nucleic acid sequencing.

BACKGROUND

A variety of types of chemical sensors have been used in the detection of chemical processes. One type is a chemically-sensitive field effect transistor (chemFET). A chemFET includes a source and a drain separated by a channel region, and a chemically sensitive area coupled to the channel region. The operation of the chemFET is based on the modulation of channel conductance, caused by changes in charge at the sensitive area due to a chemical reaction occurring nearby. The modulation of the channel conductance changes the threshold voltage of the chemFET, which can be measured to detect and/or determine characteristics of the chemical reaction. The threshold voltage may for example be measured by applying appropriate bias voltages to the source and drain, and measuring a resulting current flowing through the chemFET. As another example, the threshold voltage may be measured by driving a known current through the chemFET, and measuring a resulting voltage at the source or drain.

An ion-sensitive field effect transistor (ISFET) is a type of chemFET that includes an ion-sensitive layer at the sensitive area. The presence of ions in an analyte solution alters the surface potential at the interface between the ion-sensitive layer and the analyte solution, due to the protonation or deprotonation of surface charge groups caused by the ions present in the analyte solution. The change in surface potential at the sensitive area of the ISFET affects the threshold voltage of the device, which can be measured to indicate the presence and/or concentration of ions within the solution.

Arrays of ISFETs may be used for monitoring chemical reactions, such as DNA sequencing reactions, based on the detection of ions present, generated, or used during the reactions. See, for example, U.S. Pat. No. 7,948,015 to Rothberg et al., which is incorporated by reference herein in its entirety. More generally, large arrays of chemFETs or other types of chemical sensors may be employed to detect and measure static and/or dynamic amounts or concentrations of a variety of analytes (e.g. hydrogen ions, other ions, compounds, etc.) in a variety of processes. The processes may for example be biological or chemical reactions, cell or tissue cultures or monitoring neural activity, nucleic acid sequencing, etc.

An issue that arises in the operation of large scale chemical sensor arrays is the susceptibility of the sensor output signals to noise. Specifically, the noise affects the accuracy of the downstream signal processing used to determine the characteristics of the chemical and/or biological process being detected by the sensors.

It is therefore desirable to provide methods for reducing noise in output signals of chemical sensors and improving signal to noise ratio and readout of chemical sensors.

SUMMARY

In one implementation, a method is described. The method includes determining an operational characteristic of sensors of a sensor array. The method further includes selecting a group of sensors in the array based on the operational characteristic of sensors in the group. The method further includes enabling readout of the sensors in the selected group. The method further includes receiving output signals from the enabled sensors, the output signals indicating chemical reactions occurring proximate to the sensors of the sensor array.

In one embodiment, the operational characteristic of sensors of a sensor array is selected from the group of a bead loading quality of the sensors of the sensor array, a noise spectrum of the sensors of the sensor array, and a threshold voltage value of the sensors of the sensor array. In another embodiment, readout of remaining sensors of the sensor array is bypassed. According to another embodiment, the selecting a group of sensors in the array is based on more than one operational characteristic of sensors in the group. In a further embodiment, the sensors in the sensor array include chemically-sensitive field effect transistors. According to once embodiment, the chemically-sensitive field effect transistors are arranged in rows and columns and the selecting includes selecting contiguous rows of chemically-sensitive field effect transistors in the sensor array. In another embodiment, the output signals further indicate an ion concentration due to sequencing reactions occurring proximate to the chemically-sensitive field effect transistors. According to one embodiment, the output signals are analog signals and the method further includes converting the output signals into digital signals and the receiving output signals further includes receiving the converted digital signals.

In another implementation, a method for nucleic acid sequencing is described. The method includes providing template nucleic acids to at least some of a plurality of locations coupled to sensors of an array. The method further includes analyzing output signals of the sensors of the array to identify which locations in the plurality of locations contain the disposed template nucleic acids. The method further includes selecting a group of sensors coupled to identified locations containing the disposed template nucleic acids. The method further includes introducing known nucleotides within at least some of the plurality of locations. The method further includes measuring the output signals of the selected sensors to detect sequencing reaction byproducts resulting from incorporation of the introduced known nucleotides into one of more primers hybridized to at least one of the disposed template nucleic acids.

In one embodiment, the method further comprises enabling readout of the sensors in the selected group, and bypassing readout of remaining sensors of the sensor array. In another embodiment, the sequencing reaction byproducts comprise hydrogen ions. In yet another embodiment, the sequencing reaction byproducts resulting from incorporation are of chemically similar composition for each of the known nucleotides. In one embodiment, the method further comprises determining at least a portion of sequences of at least a portion of the template nucleic acids based on the introduced known nucleotides and further based on the measured output signals. According to one embodiment, the sensors comprise field-effect transistors having a chemically sensitive portion responsive to the sequencing reaction byproducts and disposed in proximity to the locations such that the at least one of the sequencing reaction byproducts diffuse or contact the sensors to thereby be detected. According to another embodiment, the chemically sensitive portion of the field-effect transistors of the array is responsive to a plurality of different sequencing reaction byproducts. In yet another embodiment, the locations are within respective reaction chambers. In one embodiment, the measured output signals are analog signals and the method further includes converting the output signals into digital signals and the receiving output signals further includes receiving the converted digital signals.

Particular aspects of one more implementations of the subject matter described in this specification are set forth in the drawings and the description below. Other features, aspects, and advantages of the subject matter will become apparent from the description, the drawings, and the claims.

DETAILED DESCRIPTION

Methods for reducing noise in output signals of chemical sensors and improving readout of output signal of chemical sensors based on the operational characteristic of the chemical sensors are described. For example, an integrated circuit may comprise an array of chemically sensitive sensors arranged in rows and columns. Output signals from the sensors indicating chemical reactions occurring proximate to the sensors of the sensor array may be read out. Determining an operational characteristic of sensors of a sensor array before the chemical reactions occur and reading out sensors based on the determined operational characteristic results in improved signal quality of output signals, for example.

Figure 1:
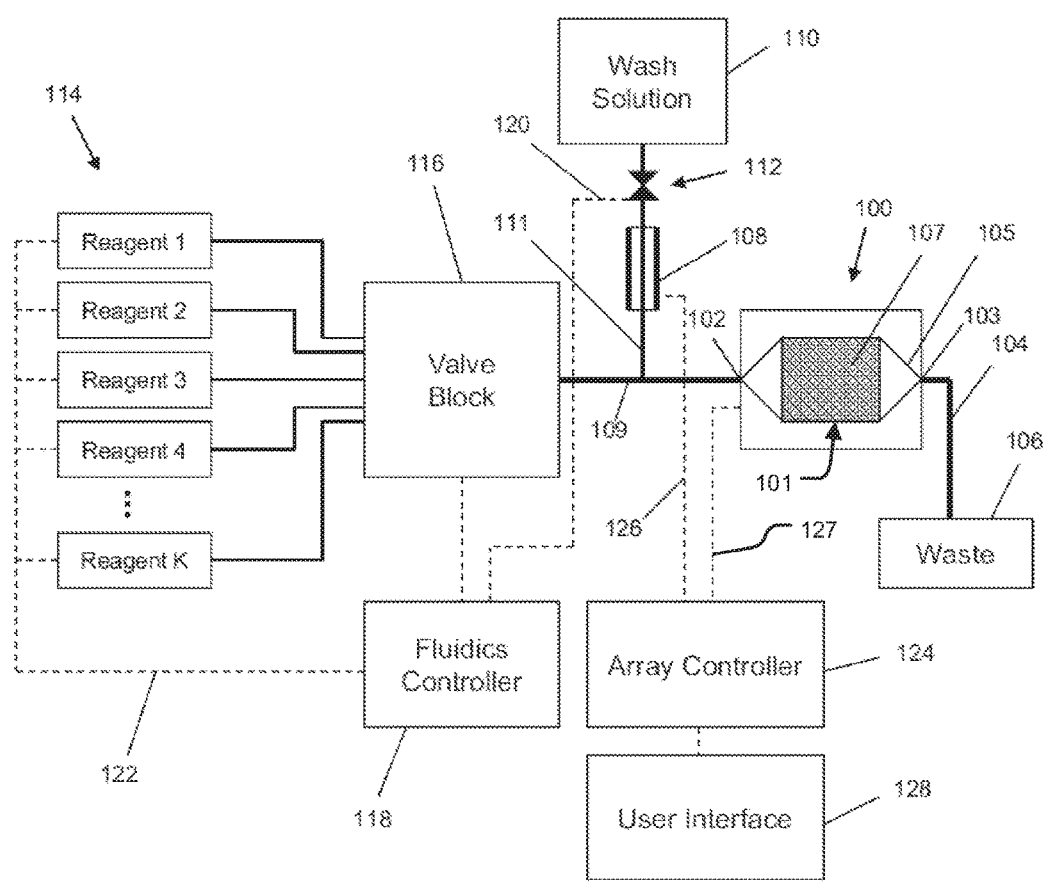
FIG. 1 illustrates a block diagram of components of a system for nucleic acid sequencing according to an exemplary embodiment.

FIG. 1 illustrates a block diagram of components of a system for nucleic acid sequencing according to an exemplary embodiment. The components include flow cell 101 on integrated circuit device 100, reference electrode 108, plurality of reagents 114 for sequencing, valve block 116, wash solution 110, valve 112, fluidics controller 118, lines 120/122/126, passages 104/109/111, waste container 106, array controller 124, and user interface 128. Integrated circuit device 100 includes microwell array 107 overlying a sensor array that includes chemical sensors as described herein. Flow cell 101 includes inlet 102, outlet 103, and flow chamber 105 defining a flow path for reagents over microwell array 107. Reference electrode 108 may be of any suitable type or shape, including a concentric cylinder with a fluid passage or a wire inserted into a lumen of passage 111. Reagents 114 may be driven through the fluid pathways described above, valve block 116 and valve 112, and flow cell 101 by pumps, gas pressure, or other suitable methods, and may be discarded into waste container 106 after exiting outlet 103 of flow cell 101. Fluidics controller 118 may control driving forces for reagents 114 and the operation of valve 112 and valve block 116 with suitable software. Flow cell 101 may have a variety of configurations for controlling the path and flow rate of reagents 114 over microwell array 107. Array controller 124 provides bias voltages and timing and control signals to integrated circuit device 100 for reading the chemical sensors of the sensor array. Array controller 124 also provides a reference bias voltage to reference electrode 108 to bias reagents 114 flowing over microwell array 107. Microwell array 107 includes an array of reaction regions as described herein, also referred to herein as microwells, which are operationally associated with corresponding chemical sensors in the sensor array. For example, each reaction region may be coupled to a chemical sensor suitable for detecting an analyte or reaction property of interest within that reaction region. Microwell array 107 may be integrated in integrated circuit device 100, so that microwell array 107 and the sensor array are part of a single device or chip.

During an experiment, array controller 124 collects and processes output signals from the chemical sensors of the sensor array through output ports on integrated circuit device 100 via bus 127. Array controller 124 may be a computer or other computing means. Array controller 124 may include memory for storage of data and software applications, a processor for accessing data and executing applications, and components that facilitate communication with the various components of the system in FIG. 1. The values of the output signals of the chemical sensors indicate physical and/or chemical parameters of one or more reactions taking place in the corresponding reaction regions in microwell array 107. For example, in an exemplary embodiment, the values of the output signals may be processed using the techniques disclosed in Rearick et al., U.S. patent application Ser. No. 13/339,846, filed Dec. 29, 2011, based on U.S. Prov. Pat. Appl. Nos. 61/428,743, filed Dec. 30, 2010, and 61/429,328, filed Jan. 3, 2011, and in Hubbell, U.S. patent application Ser. No. 13/339,753, filed Dec. 29, 2011, based on U.S. Prov. Pat. Appl. No 61/428,097, filed Dec. 29, 2010, each which are incorporated by reference herein in their entirety. User interface 128 may display information about flow cell 101 and the output signals received from chemical sensors in the sensor array on integrated circuit device 100. User interface 128 may also display instrument settings and controls, and allow a user to enter or set instrument settings and controls.

In an exemplary embodiment, during the experiment fluidics controller 118 may control delivery of individual reagents 114 to flow cell 101 and integrated circuit device 100 in a predetermined sequence, for predetermined durations, at predetermined flow rates. Array controller 124 can then collect and analyze the output signals of the chemical sensors indicating chemical reactions occurring in response to the delivery of reagents 114. During the experiment, the system may also monitor and control the temperature of integrated circuit device 100, so that reactions take place and measurements are made at a known predetermined temperature. The system may be configured to let a single fluid or reagent contact reference electrode 108 throughout an entire multi-step reaction during operation. Valve 112 may be shut to prevent any wash solution from flowing into passage 109 as reagents 114 are flowing. Although the flow of wash solution may be stopped, there may still be uninterrupted fluid and electrical communication between reference electrode 108, passage 109, and microwell array 107. The distance between reference electrode 108 and junction between passages 109 and 111 may be selected so that little or no amount of the reagents flowing in passage 109 and possibly diffusing into passage 111 reach reference electrode 108. In an exemplary embodiment, wash solution 110 may be selected as being in continuous contact with reference electrode 108, which may be especially useful for multi-step reactions using frequent wash steps.

Figure 2:
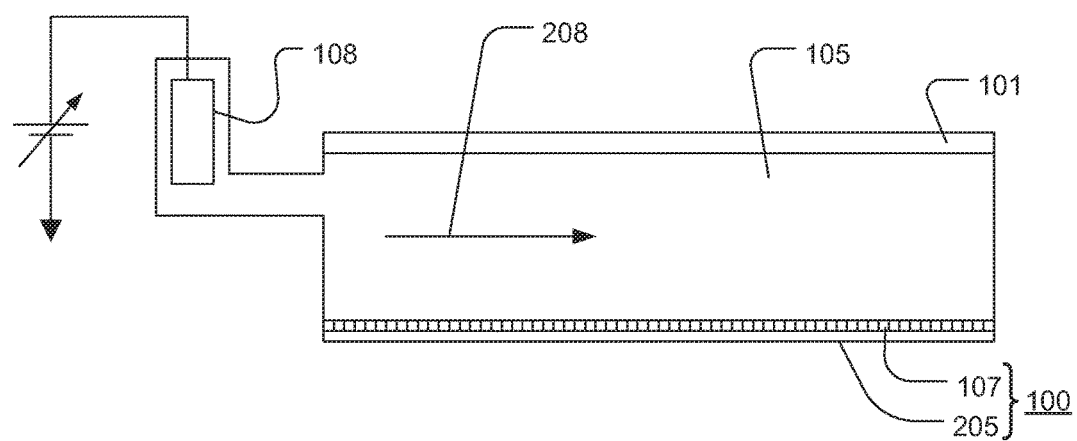
FIG. 2 illustrates a cross-sectional view of a portion of the integrated circuit device and flow cell according to an exemplary embodiment.

FIG. 2 illustrates cross-sectional and expanded views of a portion of integrated circuit device 100 and flow cell 101. During operation, flow chamber 105 of flow cell 101 confines reagent flow 208 of delivered reagents across open ends of the reaction regions in microwell array 107. The volume, shape, aspect ratio (such as base width-to-well depth ratio), and other dimensional characteristics of the reaction regions may be selected based on the nature of the reaction taking place, as well as the reagents, byproducts, or labeling techniques (if any) that are employed. The chemical sensors of sensor array 205 are responsive to (and generate output signals to) chemical reactions within associated reaction regions in microwell array 107 to detect an analyte or reaction property of interest. The chemical sensors of sensor array 205 may for example be chemically sensitive field-effect transistors (chemFETs), such as ion-sensitive field effect transistors (ISFETs). Examples of chemical sensors and array configurations that may be used in embodiments are described in U.S. Patent Application Publication No. 2010/0300559, No. 2010/0197507, No. 2010/0301398, No. 2010/0300895, No. 2010/0137143, and No. 2009/0026082, and U.S. Pat. No. 7,575,865, each which are incorporated by reference herein in their entirety.

Figure 3:
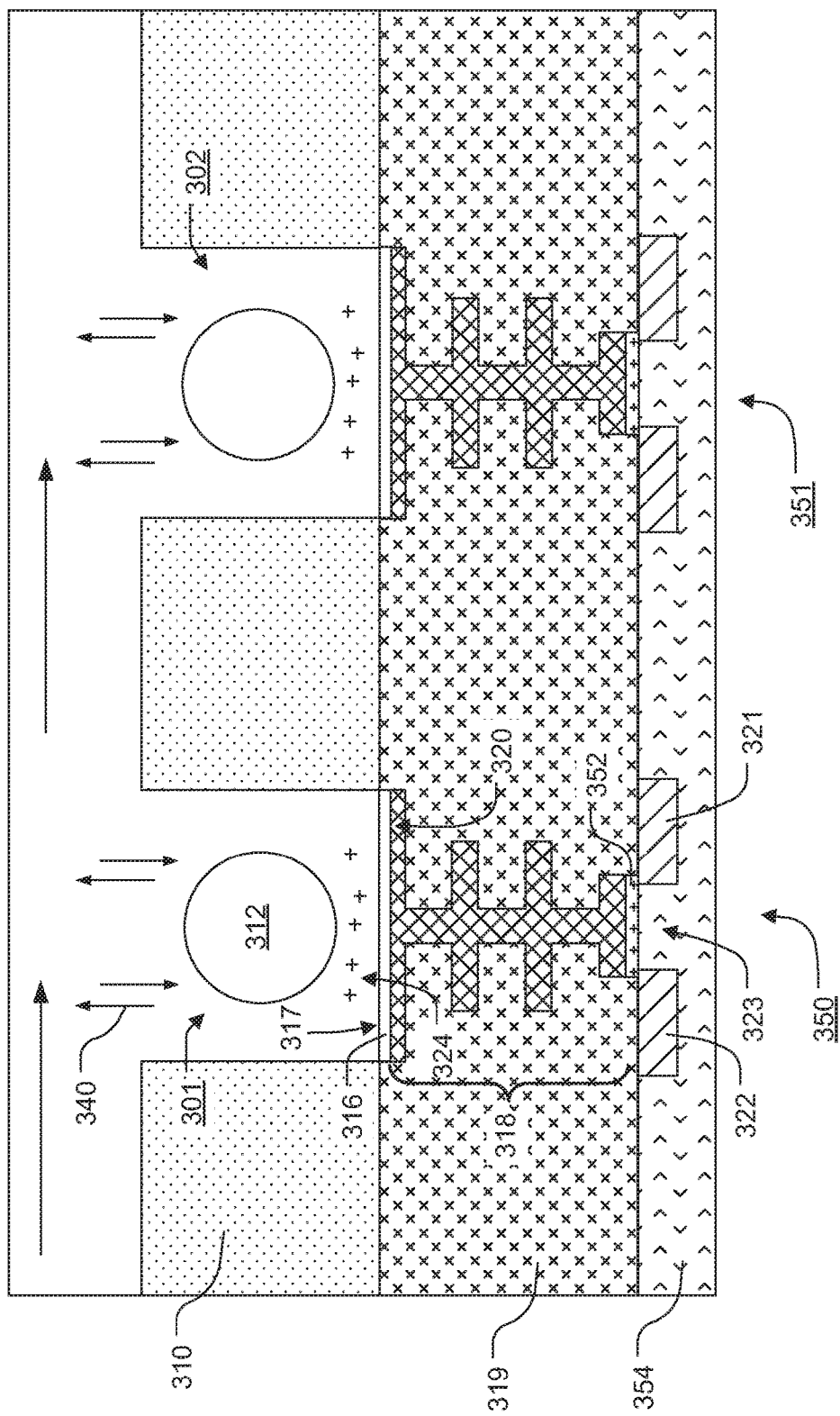
FIG. 3 illustrates a cross-sectional view of representative chemical sensors and corresponding reaction regions according to an exemplary embodiment.

FIG. 3 illustrates a cross-sectional view of two representative chemical sensors and their corresponding reaction regions according to an exemplary embodiment. In FIG. 3, two chemical sensors 350, 351 are shown, representing a small portion of a sensor array that can include millions of chemical sensors. Chemical sensor 350 is coupled to corresponding reaction region 301, and chemical sensor 351 is coupled to corresponding reaction region 302. Chemical sensor 350 is representative of the chemical sensors in the sensor array. In the illustrated example, chemical sensor 350 is an ion-sensitive field effect transistor. Chemical sensor 350 includes floating gate structure 318 having a floating gate conductor (referred to herein as the sensor plate) separated from reaction region 301 by sensing material 316. As shown in FIG. 3, sensor plate 320 is the uppermost patterned layer of conductive material in floating gate structure 318 underlying reaction region 301.

In the illustrated example, floating gate structure 318 includes multiple patterned layers of conductive material within layers of dielectric material 319. The upper surface of sensing material 316 acts as sensing surface 317 for chemical sensor 350. In the illustrated embodiment, sensing material 316 is an ion-sensitive material, such that the presence of ions or other charged species in a solution in the reaction region 301 alters the surface potential of sensing surface 317. The change in the surface potential is due to the protonation or deprotonation of surface charge groups at the sensing surface caused by the ions present in the solution. The sensing material may be deposited using various techniques, or naturally formed during one or more of the manufacturing processes used to form chemical sensor 350. In some embodiments, sensing material 316 is a metal oxide, such as an oxide of silicon, tantalum, aluminum, lanthanum, titanium, zirconium, hafnium, tungsten, palladium, iridium, etc, or any other suitable metal oxide, or combination thereof. In some embodiments, sensing material 316 is an oxide of the upper layer of conductive material of sensor plate 320. For example, the upper layer of sensor plate 320 may be titanium nitride, and sensing material 316 may comprise titanium oxide or titanium oxynitride. More generally, sensing material 316 may comprise one or more of a variety of different materials to facilitate sensitivity to particular ions. For example, silicon nitride or silicon oxynitride, as well as metal oxides such as silicon oxide, aluminum or tantalum oxides, generally provide sensitivity to hydrogen ions, whereas sensing materials comprising polyvinyl chloride containing valinomycin provide sensitivity to potassium ions. Materials sensitive to other ions such as sodium, silver, iron, bromine, iodine, calcium, and nitrate may also be used, depending upon the implementation.

The chemical sensor also includes source region 321 and drain region 322 within semiconductor substrate 354. Source region 321 and drain region 322 comprise doped semiconductor material have a conductivity type different from the conductivity type of substrate 354. For example, source region 321 and drain region 322 may comprise doped P-type semiconductor material, and the substrate may comprise doped N-type semiconductor material. Channel region 323 separates source region 321 from drain region 322. Floating gate structure 318 overlies channel region 323, and is separated from substrate 354 by gate dielectric 352. Gate dielectric 352 may be for example silicon dioxide. Alternatively, other suitable dielectrics may be used for gate dielectric 352. Reaction region 301 extends through fill material 310 on dielectric material 319. The fill material may for example comprise one or more layers of dielectric material, such as silicon dioxide or silicon nitride. Sensor plate 320, sensing material 316 and reaction region 301 may for example have circular cross-sections. Alternatively, these may be non-circular. For example, the cross-section may be square, rectangular, hexagonal, or irregularly shaped. The device in FIG. 3 can also include additional elements such as array lines (e.g. word lines, bit lines, etc.) for accessing the chemical sensors, additional doped regions in substrate 354, and other circuitry (e.g. access circuitry, bias circuitry etc.) used to operate the chemical sensors, depending upon the device and array configuration in which the chemical sensors described herein are implemented. In some embodiments, the device may for example be manufactured using techniques described in U.S. Patent Application Publication No. 2010/0300559, No. 2010/0197507, No. 2010/0301398, No. 2010/0300895, No. 2010/0137143, and No. 2009/0026082, and U.S. Pat. No. 7,575,865, each which are incorporated by reference herein in their entirety.

In operation, reactants, wash solutions, and other reagents may move in and out of reaction region 301 by diffusion mechanism 340. Chemical sensor 350 is responsive to (and generates an output signal related to) the amount of charge 324 present on sensing material 316 opposite sensor plate 320. Changes in charge 324 cause changes in the voltage on floating gate structure 318, which in turn changes in the threshold voltage of the transistor. This change in threshold voltage can be measured by measuring the current in channel region 323 between source region 321 and drain region 322. As a result, chemical sensor 350 can be used directly to provide a current-based output signal on an array line connected to source region 321 or drain region 322, or indirectly with additional circuitry to provide a voltage-based output signal. In an embodiment, reactions carried out in reaction region 301 can be analytical reactions to identify or determine characteristics or properties of an analyte of interest. Such reactions can generate directly or indirectly byproducts that affect the amount of charge adjacent to sensor plate 320. If such byproducts are produced in small amounts or rapidly decay or react with other constituents, multiple copies of the same analyte may be analyzed in reaction region 301 at the same time in order to increase the output signal generated. In an embodiment, multiple copies of an analyte may be attached to solid phase support 312, either before or after deposition into reaction region 301. The solid phase support may be microparticles, nanoparticles, beads, solid or porous gels, or the like. For simplicity and ease of explanation, solid phase support may also be referred herein as a particle. For a nucleic acid analyte, multiple, connected copies may be made by rolling circle amplification (RCA), exponential RCA, Recombinase Polymerase Amplification (RPA), Polymerase Chain Reaction amplification (PCR), emulsion PCR amplification, or like techniques, to produce an amplicon without the need of a solid support.

Figure 4:
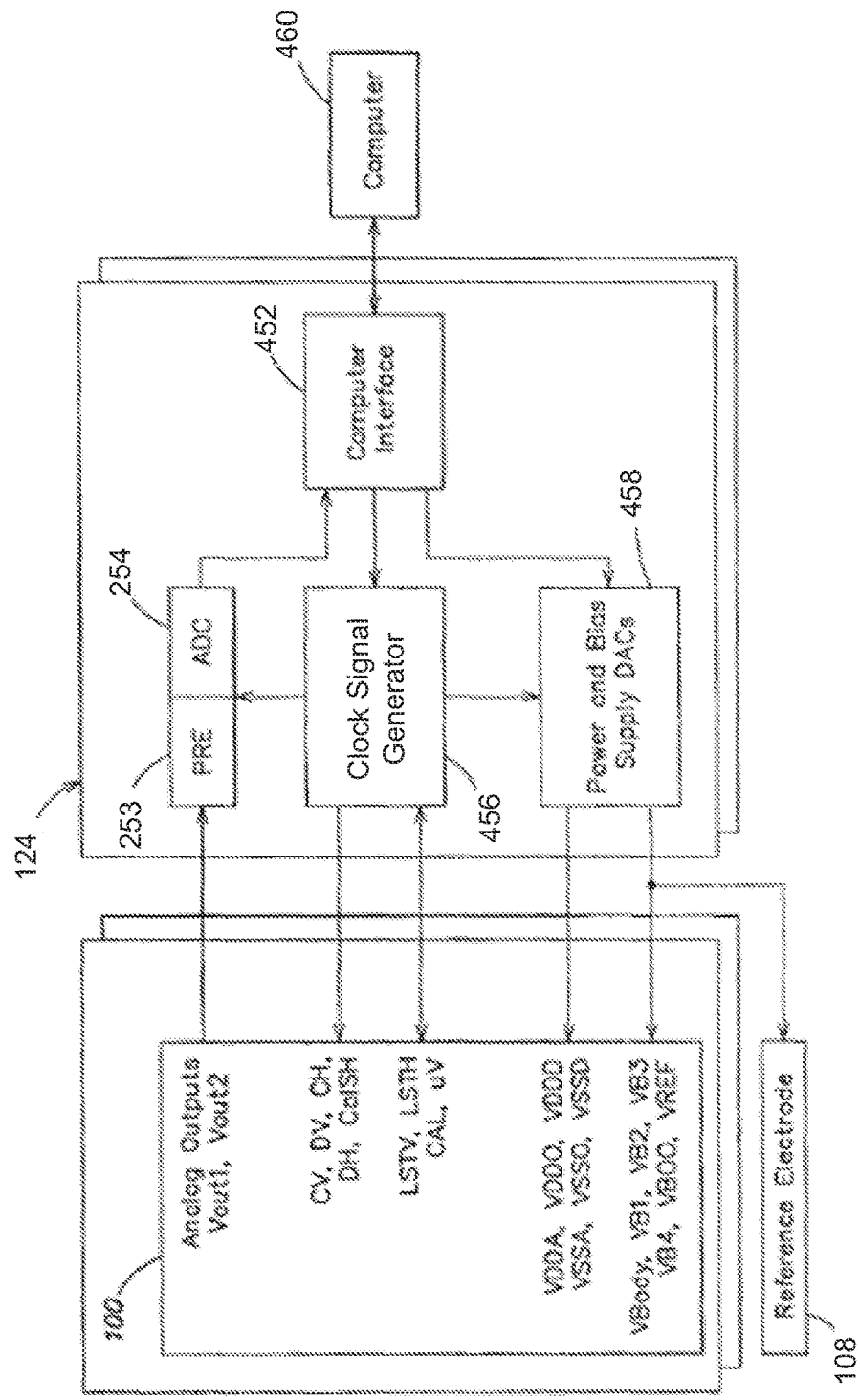
FIG. 4 illustrates a block diagram of an exemplary chemical sensor array of coupled to an array controller, according to an exemplary embodiment.

FIG. 4 illustrates a block diagram of an exemplary chemical sensor array coupled to an array controller, according to an exemplary embodiment. In various exemplary implementations, array controller 124 may be fabricated as a "stand alone" controller, or as a computer compatible "card" forming part of a computer 460, (See FIG. 8 in U.S. Pat. No. 7,948,015 for further details, which is incorporated by reference in its entirety herein). In one aspect, the functions of the array controller 124 may be controlled by computer 460 through an interface block 452 (e.g., serial interface, via USB port or PCI bus, Ethernet connection, etc.), as shown in FIG. 4. In one embodiment, array controller 124 is fabricated as a printed circuit board into which integrated circuit device 100 plugs; similar to a conventional IC chip (e.g., integrated circuit device 100 is configured as an ASIC that plugs into the array controller). In one aspect of such an embodiment, all or portions of array controller 124 may be implemented as a field programmable gate array (FPGA) configured to perform various array controller functions. For example, having determined an operational characteristic of sensors of the sensor array, the FPGA may be configured to select a group of sensors in the array based on the operational characteristic of sensors in the group and enable readout of the sensors in the selected group. Suitable readout circuitry may receive output signals from the enabled sensors, the output signals indicating chemical reactions occurring proximate to the sensors of the sensor array.

Generally, array controller 124 provides various supply voltages and bias voltages to integrated circuit device 100, as well as various signals relating to row and column selection, sampling of pixel outputs and data acquisition. In particular, array controller 124 reads the two analog output signals Vout1 (for example, odd columns) and Vout2 (for example, even columns) including multiplexed respective pixel voltage signals from integrated circuit device 100 and then digitizes these respective pixel signals to provide measurement data to computer 460, which in turn may store and/or process the data. In some implementations, array controller 124 also may be configured to perform or facilitate various array calibration and diagnostic functions, and an optional array UV irradiation treatment (See FIG. 11A in U.S. Pat. No. 7,948,015, which is incorporated by reference in its entirety herein, for further details). In general, the array controller provides the integrated circuit device with the analog supply voltage and ground (VDDA, VSSA), the digital supply voltage and ground (VDDD, VSSD), and the buffer output supply voltage and ground (VDDO, VSSO). In one exemplary implementation, each of the supply voltages VDDA, VDDD and VDDO is approximately 3.3 Volts.

As discussed above, in one aspect each of these power supply voltages is provided to integrated circuit device 100 via separate conducting paths to facilitate noise isolation. In another aspect, these supply voltages may originate from respective power supplies/regulators, or one or more of these supply voltages may originate from a common source in power supply 458 of array controller 124. Power supply 458 also may provide the various bias voltages required for array operation (e.g., VB1, VB2, VB3, VB4, VBO0, $V_{BODY}$) and the reference voltage VREF used for array diagnostics and calibration. In another aspect, power supply 458 includes one or more digital-to-analog converters (DACs) that may be controlled by computer 460 to allow any or all of the bias voltages, reference voltage, and supply voltages to be changed under software control (i.e., programmable bias settings). For example, power supply 458 responsive to computer control may facilitate adjustment of the bias voltages VB1 and VB2 for pixel drain current, VB3 for column bus drive, VB4 for column amplifier bandwidth, and VBO0 for column output buffer current drive. In some aspects, one or more bias voltages may be adjusted to optimize settling times of signals from enabled pixels. Additionally, the common body voltage $V_{BODY}$ for all ISFETs of the array may be grounded during an optional post-fabrication UV irradiation treatment to reduce trapped charge, and then coupled to a higher voltage (e.g., VDDA) during diagnostic analysis, calibration, and normal operation of the array for measurement/data acquisition. Likewise, the reference voltage VREF may be varied to facilitate a variety of diagnostic and calibration functions. Reference electrode 108 which is typically employed in connection with an analyte solution to be measured by integrated circuit device 100 (See FIG. 1 in U.S. Pat. No. 7,948,015, which is incorporated by reference in its entirety herein, for further details), may be coupled to power supply 458 to provide a reference potential for the pixel output voltages. For example, in one implementation reference electrode 108 may be coupled to a supply ground (e.g., the analog ground VSSA) to provide a reference for the pixel output voltages based on Eq. (3) in U.S. Pat. No. 7,948,015. In one exemplary implementation, the reference electrode voltage may be set by placing a solution/sample of interest having a known pH level in proximity to integrated circuit device 100 and adjusting the reference electrode voltage until the array output signals Vout1 and Vout2 provide pixel voltages at a desired reference level, from which subsequent changes in pixel voltages reflect local changes in pH with respect to the known reference pH level. In general, it should be appreciated that a voltage associated with reference electrode 108 need not necessarily be identical to the reference voltage VREF discussed in U.S. Pat. No. 7,948,015 (which may be employed for a variety of array diagnostic and calibration functions), although in some implementations the reference voltage VREF provided by power supply 458 may be used to set the voltage of reference electrode 108.

Regarding data acquisition from integrated circuit device 100, in one embodiment array controller 124 of FIG. 4 may include one or more preamplifiers 253 to further buffer the output signals Vout1 and Vout2 from the sensor array and provide selectable gain. In one implementation, array controller 124 may include one preamplifier for each output signal (e.g., two preamplifiers for two analog output signals). In other aspects, the preamplifiers may be configured to accept input voltages from 0.0 to 3.3 Volts or from 0.1 to 5.0 Volts, may have programmable/computer selectable gains (e.g., 1, 2, 5, 10 and 20) and low noise outputs (e.g., <10 nV/sqrtHz), and may provide low pass filtering (e.g., bandwidths of 5 MHz and 25 MHz). In yet another implementation, the preamplifiers may have a programmable/computer selectable offset for input and/or output voltage signals to set a nominal level for either to a desired range. The array controller 124 may also comprise one or more analog-to-digital converters 454 (ADCs) to convert the sensor array output signals Vout1 and Vout2 to digital outputs (e.g., 10-bit or 12-bit) so as to provide data to computer 460. In one aspect, one ADC may be employed for each analog output of the integrated circuit device, and each ADC may be coupled to the output of a corresponding preamplifier (if preamplifiers are employed in a given implementation). In another aspect, the ADC(s) may have a computer-selectable input value ranging from 50 mV to 1 Volt, for example (e.g., 50 mV, 200 mV, 500 mV, 1 V) to facilitate compatibility with different ranges of array output signals and/or preamplifier parameters. In yet other aspects, the bandwidth of the ADC(s) may be greater than 60 MHz, and the data acquisition/conversion rate greater than 25 MHz (e.g., as high as 100 MHz or greater). ADC acquisition timing and array row and column selection may be controlled by timing generator 456. In particular, the timing generator provides the digital vertical data and clock signals (DV, CV) to control row selection, the digital horizontal data and clock signals (DH, CH) to control column selection, and the column sample and hold signal COL SH to sample respective pixel voltages for an enabled row. (See FIG. 9 in U.S. Pat. No. 7,948,015, which is incorporated by reference in its entirety herein, for further details). In one implementation, timing generator 456 may be implemented by a microprocessor executing code and configured as a multi-channel digital pattern generator to provide appropriately timed control signals. For example, timing generator 456 may be implemented as a field-programmable gate array (FPGA). For further details of row and column circuitry, see U.S. Pat. No. 7,948,015, which is incorporated by reference in its entirety herein.

Figure 5:
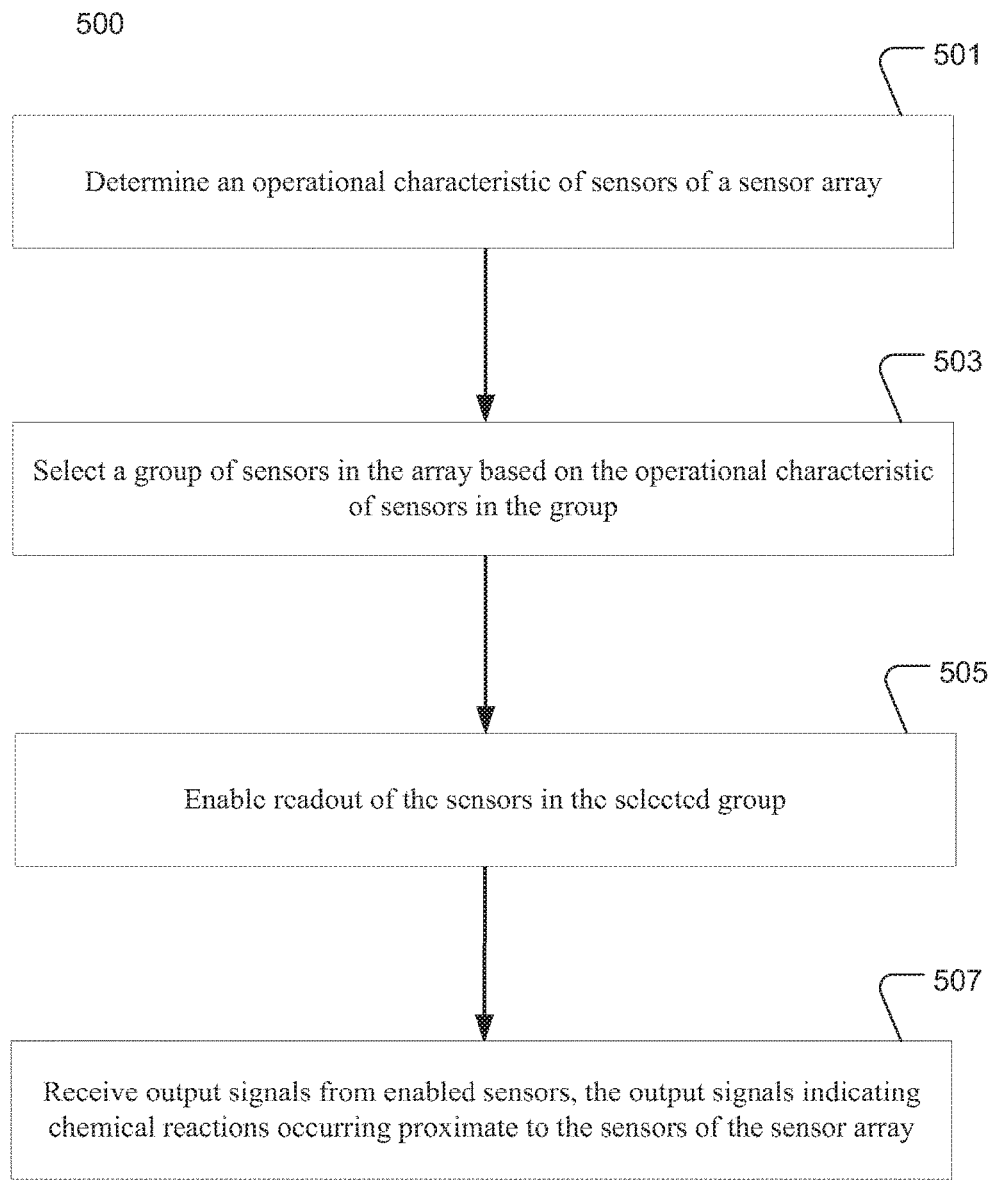
FIG. 5 illustrates a method, according to an exemplary embodiment.

FIG. 5 illustrates a method 500 according to an exemplary embodiment of how various operational characteristics of sensors of a sensor array may be taken into consideration during a read operation of the sensor array. In step 501, at least one operational characteristic of an individual sensor, a group of sensors, or all sensors of a sensor array is determined. Examples of operational characteristics of sensors include, but are not limited to, bead loading quality, a noise spectrum, and a threshold voltage value, and any combinations thereof. In step 503, a group of sensors in the array based on the operational characteristic of sensors in the group may be selected. The selecting a group of sensors in the array may be based on more than one operational characteristic of sensors in the group. In step 505, readout of the sensors in the selected group may be enabled. According to exemplary embodiments, readout of remaining sensors of the sensor array may be bypassed. In step 507, output signals from the enabled sensors may be received, the output signals indicating chemical reactions occurring proximate to the sensors of the sensor array. Sensors in the sensor array may include chemically-sensitive field effect transistors. The chemically-sensitive field effect transistors may be arranged in rows and columns and the selecting includes selecting contiguous rows of chemically-sensitive field effect transistors in the sensor array. During an experiment, a fluidics controller may deliver individual reagents to the flow cell and integrated circuit device in a predetermined sequence. The output signals may indicate an ion concentration due to sequencing reactions occurring proximate to the chemically-sensitive field effect transistors. In an exemplary implementation, the output signals may be analog signals and the method may further include converting the output signals into digital signals and the receiving output signals may further include receiving the converted digital signals.

Figure 6:
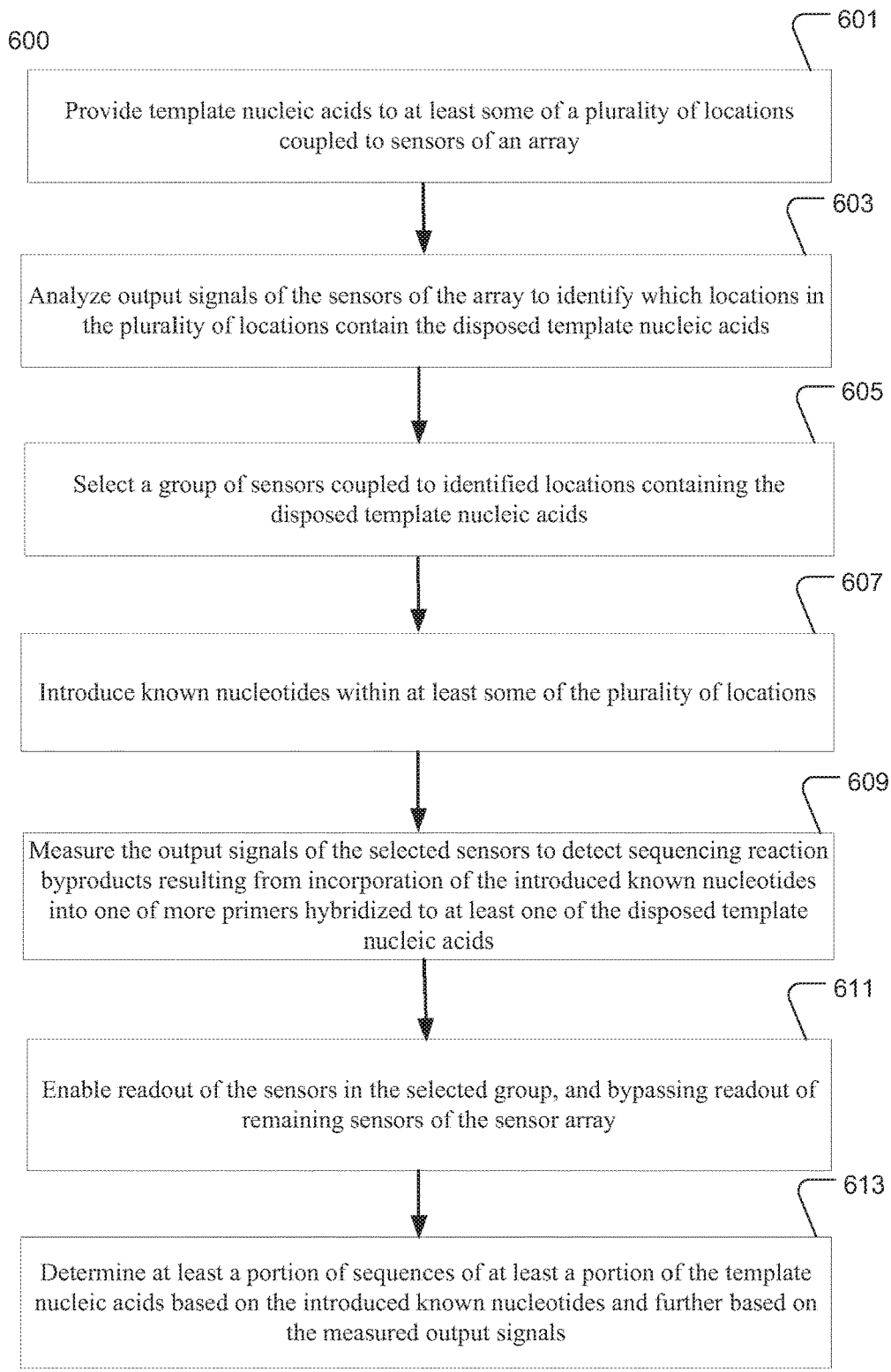
FIG. 6 illustrates a method for nucleic acid sequencing, according to an exemplary embodiment.

FIG. 6 illustrates a method 600 for nucleic acid sequencing according to an exemplary implementation. In step 601, template nucleic acids may be provided to at least some of a plurality of locations coupled to sensors of an array. In step 603, output signals of the sensors of the array may be analyzed to identify which locations in the plurality of locations contain the disposed template nucleic acids. In step 605, a group of sensors coupled to the identified locations containing the disposed template nucleic acids may be selected. In step 607, known nucleotides within at least some of the plurality of locations may be introduced. In step 609, the output signals of the selected sensors may be measured to detect sequencing reaction byproducts resulting from incorporation of the introduced known nucleotides into one of more primers hybridized to at least one of the disposed template nucleic acids. The sequencing reaction byproducts may comprise, for example, hydrogen ions, hydroxide ions, other ions, inorganic pyrophosphates (PPi), or any other suitable reaction byproduct or combination thereof. The sequencing reaction byproducts resulting from incorporation may be of chemically similar composition for each of the known nucleotides and sensors in the array detect a same byproduct. In step 611, readout of the sensors in the selected group, and bypassing readout of remaining sensors of the sensor array may be enabled. In step 613, at least a portion of sequences of at least a portion of the template nucleic acids may be determined based on the introduced known nucleotides and further based on the measured output signals. The sensors may comprise field-effect transistors having a chemically sensitive portion responsive to the sequencing reaction byproducts and may be disposed in proximity to the locations such that the at least one of the sequencing reaction byproducts diffuse or contact the sensors to thereby be detected. The chemically sensitive portion of the field-effect transistors of the array is responsive to a plurality of different sequencing reaction byproducts. The locations may be within respective reaction chambers. The measured output signals may be analog signals and the method may further include converting the output signals into digital signals and the receiving output signals may further include receiving the converted digital signals.

Figure 7:
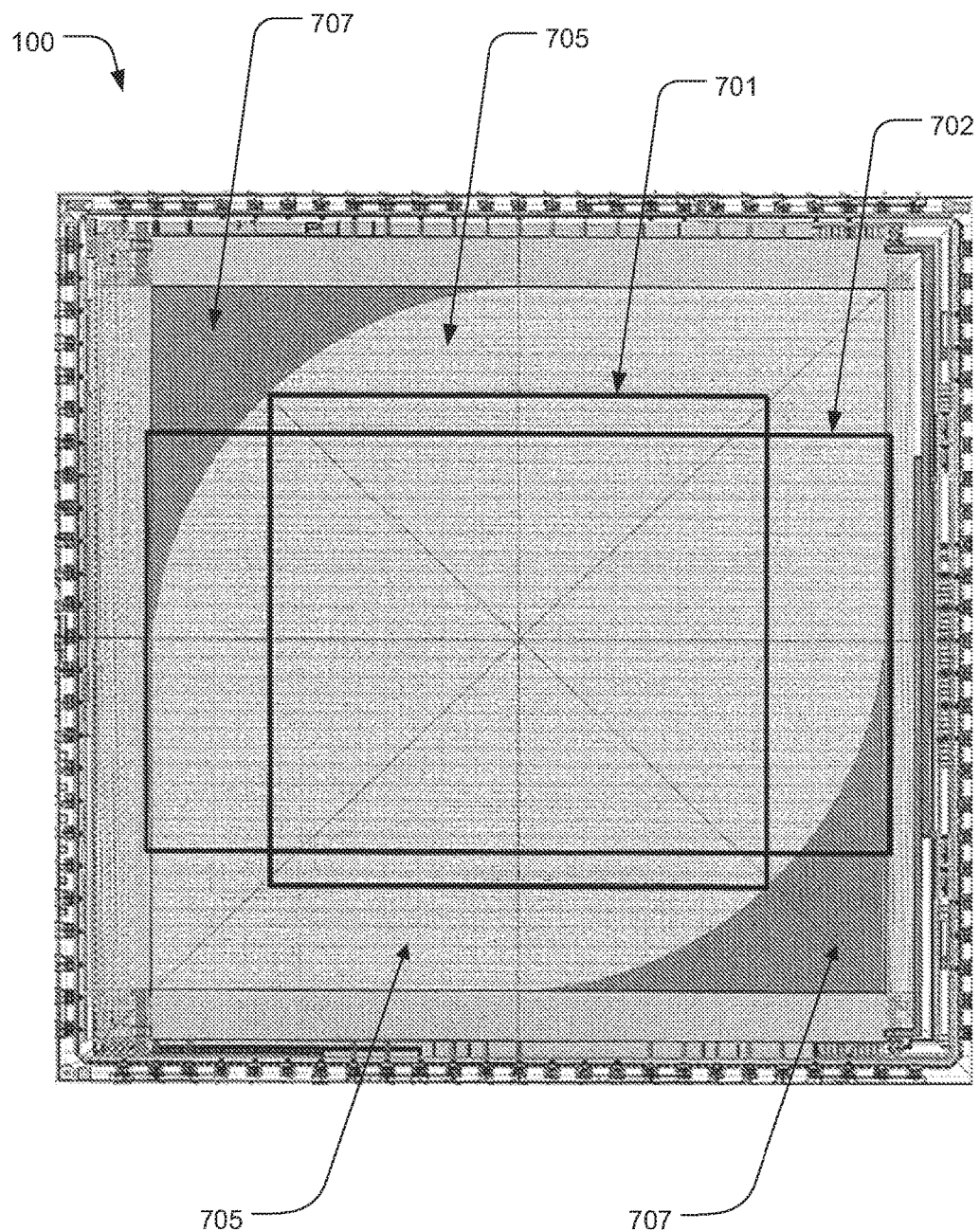
FIG. 7 illustrates examples of two different groups of sensors in an array that have been selected based on an operational characteristic of sensors in the group, according to an exemplary embodiment.

FIG. 7 illustrates examples of two different groups of sensors in an array on integrated circuit device 100 that have been selected based on an operational characteristic of sensors in the group. The sensors in the array illustrated in FIG. 7 are arranged in rows and columns. For example, a first group of sensors (defined by sensors within area 701) may be selected based on one (or more) operational characteristics of sensors in the group. Another group of sensors (defined by sensors within area 702) may be selected based on (a) different operational characteristic(s) of sensors in the group. The sensors within the wells may comprise fluid-addressable wells 705, and may also comprise reference wells 707. Thus, the group of sensors that is selected may be coupled to only fluid-addressable wells 705, only reference wells 707, or both fluid-addressable wells 705 and reference wells 707. In some embodiments, two or more, non-overlapping groups or partially-overlapping groups may be selected based on the same or different operational characteristics of sensors in the respective groups. Sensors in the two or more areas may be read out separately. First, sensors within area 701 may be read out, followed by sensors within area 702, or vice versa. Sensors within area 701 and 702 may be read out at the same time, while maintaining correspondence between the output signals and their respective sensors within a defined area (701/702, for example). The output signals from two or more corresponding areas may be compared with one another to determine which area provides an improved signal based on location of sensors on the array and/or based on the same or different operational characteristics of the sensors. The comparison may be used to predict high performance/preferred areas (sensors/sensor locations) for future experiments on unused integrated circuits/sensor arrays. The group(s) of sensors, operational characteristic(s), and the addressable area on the array may be dynamically selectable during an experiment or they may be predetermined before an experiment. The number of sensors in the group selected may vary, and the shape of the area defined by selected sensors may vary.

Embodiments of the above-described system provide particular technical advantages including an improvement in signal to noise ratio, and taking advantage of various operational characteristics of sensors of a sensor array, further enabling oversampling and improved speed in readout of output signals. Note that not all of the activities described above in the general description or the examples are required, that a portion of a specific activity may not be required, and that one or more further activities may be performed in addition to those described. Still further, the order in which activities are listed are not necessarily the order in which they are performed. In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims. After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range. While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims.

The invention claimed is:

1. A method comprising:
    determining an operational characteristic of each sensor of a plurality of sensors located at a portion of a sensor array, the determining occurring before a chemical reaction occurs proximal to each sensor of the plurality of sensors located at the portion of the sensor array;
    selecting a first group of sensors from the plurality of sensors located at the portion of the sensor array, wherein the selecting is based on determining that each sensor in the first group of sensors has a similar operational characteristic;
    enabling readout of the sensors in the first group of sensors;
    bypassing readout of other sensors of the sensor array that are not included in the first group of sensors, wherein the other sensors have a different operational characteristic than the first group of sensors; and
    receiving output signals from the first group of sensors, the output signals indicating chemical reactions occurring proximate to the first group of sensors of the sensor array.

2. The method of claim 1, wherein the operational characteristic is selected from the group consisting of a bead loading quality of the sensors of the sensor array, a noise spectrum of the sensors of the sensor array, and a threshold voltage value of the sensors of the sensor array.

3. The method of claim 1, wherein the sensors in the sensor array include chemically-sensitive field effect transistors.

4. The method of claim 3, wherein the chemically-sensitive field effect transistors are arranged in rows and columns and the selecting includes selecting sensors disposed in contiguous rows of chemically-sensitive field effect transistors in the sensor array.

5. The method of claim 3, wherein the output signals further indicate an ion concentration due to sequencing reactions occurring proximate to the chemically-sensitive field effect transistors.

6. The method of claim 3, wherein the output signals are analog signals and the method further includes converting the output signals into digital signals and the receiving output signals further includes receiving the converted digital signals.

7. A method for nucleic acid sequencing, comprising:
    providing template nucleic acids to at least some of a plurality of locations coupled to sensors of an array;
    analyzing output signals of the sensors of the array to identify which locations in the plurality of locations contain the template nucleic acids and which locations in the plurality of locations do not contain the template nucleic acids;
    selecting a first group of sensors from the sensors in the array, wherein sensors in the first group of sensors are selected based on the locations containing the template nucleic acids;
    introducing known nucleotides within at least some of the plurality of locations to cause a reaction between the template nucleic acids and the known nucleotides;
    enabling readout of the sensors in the first group of sensors in the sensor array including the locations containing the template nucleic acids, and bypassing readout of other sensors of the sensor array, wherein the other sensors are in the locations not containing the template nucleic acids; and
    measuring the output signals of the first group of sensors to detect sequencing reaction byproducts resulting from incorporation of the introduced known nucleotides into one or more primers hybridized to at least one of the template nucleic acids,
wherein the first group of sensors is selected prior to the reaction between the template nucleic acids and the known nucleotides.

8. The method of claim 7, wherein the sequencing reaction byproducts comprise hydrogen ions.

9. The method of claim 7, wherein the sequencing reaction byproducts resulting from incorporation are of chemically similar composition for each of the known nucleotides.

10. The method of claim 7, further comprising determining at least a portion of sequences of at least a portion of the template nucleic acids based on the introduced known nucleotides and further based on the measured output signals.

11. The method of claim 7, wherein the sensors comprise field-effect transistors having a chemically sensitive portion responsive to the sequencing reaction byproducts and disposed in proximity to the locations such that the at least one of the sequencing reaction byproducts diffuse or contact the sensors to thereby be detected.

12. The method of claim 11, wherein the chemically sensitive portion of the field-effect transistors of the array is responsive to a plurality of different sequencing reaction byproducts.

13. The method of claim 7, wherein the locations are within respective reaction chambers.

14. The method of claim 7, wherein the measured output signals are analog signals and the method further includes converting the measured output signals into digital signals.

15. A method comprising:
 determining an operational characteristic of a plurality of sensors located at a portion of a sensor array, the determining occurring before a chemical reaction occurs proximal to each sensor located at the portion of the sensor array;
 selecting a first group of sensors from the plurality of sensors located at the portion of the sensor array, wherein the selecting of the first group of sensors is based on determining that each sensor in the first group of sensors has a first operational characteristic;
 selecting a second group of sensors from the plurality of sensors located at the portion of the sensor array, wherein the selecting of the second group of sensors is based on determining that each sensor in the second group of sensors has a second operational characteristic, wherein the first operational characteristic and the second operational characteristic are different;
 enabling readout of the sensors in the first group of sensors and the sensors in the second group of sensors;
 comparing the readout of the sensors in the first group of sensors and the readout of the sensors in the second group of sensors; and
 receiving, based at least partially on the comparison, output signals from the first group of sensors or the second group of sensors, the output signals indicating chemical reactions occurring proximate to the sensors located at the portion of the sensor array.

16. The method of claim 15, wherein comparing the readout of the sensors in the first group of sensors and the readout of the sensors in the second group of sensors comprises:
 comparing a quality of an output signal from the sensors in the first group of sensors and a quality of an output signal from the sensors in the second group of sensors.

17. The method of claim 15, wherein the operational characteristic is selected from the group consisting of a bead loading quality of the sensors of the sensor array, a noise spectrum of the sensors of the sensor array, and a threshold voltage value of the sensors of the sensor array.

18. The method of claim 15, wherein the sensors in the sensor array include chemically-sensitive field effect transistors.

19. The method of claim 18, wherein the chemically-sensitive field effect transistors are arranged in rows and columns and the selecting a first group and the selecting a second group includes selecting sensors disposed in contiguous rows of chemically-sensitive field effect transistors in the sensor array.

20. The method of claim 15, wherein the output signals are analog signals and the method further includes converting the output signals into digital signals and the receiving output signals further includes receiving the converted digital signals.

* * * * *